(12) United States Patent
Butler et al.

(10) Patent No.: US 7,540,839 B2
(45) Date of Patent: *Jun. 2, 2009

(54) WOUND RETRACTOR

(75) Inventors: John Butler, Blackrock (IE); Frank Bonadio, Bray (IE); Michael Mulhall, Monkstown (IE); Ronan Bernard McManus, Bray (IE)

(73) Assignee: Atropos Limited, Bray, Co Wicklow (IE)

( * ) Notice: Subject to any disclaimer, the term of this patent is extended or adjusted under 35 U.S.C. 154(b) by 805 days.

This patent is subject to a terminal disclaimer.

(21) Appl. No.: 10/635,017

(22) Filed: Aug. 6, 2003

(65) Prior Publication Data

US 2004/0073090 A1    Apr. 15, 2004

Related U.S. Application Data

(63) Continuation-in-part of application No. 10/374,523, filed on Feb. 27, 2003, now Pat. No. 7,445,597, which is a continuation of application No. 09/849,341, filed on May 7, 2001, now Pat. No. 6,582,364, which is a continuation of application No. 09/688,138, filed on Oct. 16, 2000, now Pat. No. 6,254,534.

(60) Provisional application No. 60/401,023, filed on Aug. 6, 2002.

(30) Foreign Application Priority Data

Oct. 14, 1999   (IE) ........................................ 990861
Dec. 16, 1999   (IE) ........................................ 991053
Feb. 18, 2000   (EP) ................................... 00650010

(51) Int. Cl.
A61B 1/32   (2006.01)
(52) U.S. Cl. ...................................................... 600/208
(58) Field of Classification Search .......... 600/204–210
See application file for complete search history.

(56) References Cited

U.S. PATENT DOCUMENTS

| | | |
|---|---|---|
| 1,157,202 A | 10/1915 | McLeland |
| 1,598,284 A | 8/1926 | Kinney |
| 1,810,466 A | 6/1931 | Deutsch |
| 2,219,564 A | 10/1940 | Reyniers |
| 2,305,289 A | 12/1942 | Coburg |
| 2,695,608 A | 11/1954 | Gibbon |
| 2,835,253 A | 5/1958 | Borgeson |
| 2,853,075 A | 10/1958 | Hoffman |
| 3,039,468 A | 6/1962 | Price |
| 3,111,943 A | 11/1963 | Orndorff |
| 3,244,169 A | 4/1966 | Baxter |
| 3,253,594 A | 5/1966 | Matthews et al. |
| 3,313,299 A | 4/1967 | Spademan |

(Continued)

FOREIGN PATENT DOCUMENTS

DE    37 39 532    12/1988

(Continued)

*Primary Examiner*—Anu Ramana
(74) *Attorney, Agent, or Firm*—Finnegan, Henderson, Farabow, Garrett & Dunner L.L.P.

(57) ABSTRACT

A surgical wound retractor comprises a retracting member for insertion into a wound opening and a proximal member for location externally of a wound opening A clamp is used to clamp the retracting member to the proximal member.

23 Claims, 33 Drawing Sheets

U.S. PATENT DOCUMENTS

| | | |
|---|---|---|
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,656,485 A | 4/1972 | Robertson |
| 3,685,786 A | 8/1972 | Woodson |
| 3,717,151 A | 2/1973 | Collett |
| 3,729,006 A | 4/1973 | Wilder et al. |
| 3,782,370 A | 1/1974 | McDonald |
| 3,797,478 A | 3/1974 | Walsh et al. |
| 3,807,393 A | 4/1974 | McDonald |
| 3,828,764 A | 8/1974 | Jones |
| 3,841,332 A | 10/1974 | Treacle |
| 3,853,126 A | 12/1974 | Schulte |
| 3,853,127 A | 12/1974 | Spademan |
| 3,856,021 A | 12/1974 | McIntosh |
| 3,907,389 A | 9/1975 | Cox et al. |
| 3,915,171 A | 10/1975 | Shermeta |
| 3,965,890 A | 6/1976 | Gauthier |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,083,370 A | 4/1978 | Taylor |
| 4,096,853 A | 6/1978 | Weigand |
| 4,130,113 A | 12/1978 | Graham |
| 4,177,814 A | 12/1979 | Knepshield |
| 4,188,945 A | 2/1980 | Wenander |
| 4,217,664 A | 8/1980 | Faso |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lehrman |
| 4,367,728 A | 1/1983 | Mutke |
| 4,399,816 A | 8/1983 | Spangler |
| 4,411,659 A | 10/1983 | Jensen et al. |
| 4,421,296 A | 12/1983 | Stephens |
| 4,424,833 A | 1/1984 | Spector |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,485,490 A | 12/1984 | Akers et al. |
| 4,488,877 A | 12/1984 | Klein |
| 4,543,088 A | 9/1985 | Bootman |
| 4,550,713 A | 11/1985 | Hyman |
| 4,553,537 A | 11/1985 | Rosenberg |
| 4,601,710 A | 7/1986 | Moll |
| 4,610,665 A | 9/1986 | Matsumoto |
| 4,626,245 A | 12/1986 | Weinstein |
| 4,634,424 A | 1/1987 | O'Boyle |
| 4,649,904 A | 3/1987 | Krauter |
| 4,654,030 A | 3/1987 | Moll et al. |
| 4,673,393 A | 6/1987 | Suzuki et al. |
| 4,673,394 A | 6/1987 | Fenton |
| 4,755,170 A | 7/1988 | Golden |
| 4,777,943 A | 10/1988 | Chvapil |
| 4,784,646 A | 11/1988 | Feingold |
| 4,798,594 A | 1/1989 | Hillstead |
| 4,809,679 A | 3/1989 | Shimonaka |
| 4,863,438 A | 9/1989 | Gauderer |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,950,222 A | 8/1990 | Scott et al. |
| 4,950,223 A | 8/1990 | Trimark |
| 4,984,564 A | 1/1991 | Yuen |
| 4,991,593 A | 2/1991 | LeVahn |
| 4,998,538 A | 3/1991 | Charowsky et al. |
| 5,015,228 A | 5/1991 | Columbus et al. |
| 5,019,101 A | 5/1991 | Purkait |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,074,878 A | 12/1991 | Bark et al. |
| 5,082,005 A | 1/1992 | Kaldany |
| 5,092,846 A | 3/1992 | Nishijima |
| 5,125,897 A | 6/1992 | Quinn et al. |
| 5,141,498 A | 8/1992 | Christian |
| 5,149,327 A | 9/1992 | Oshiyama |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,178,162 A | 1/1993 | Bose |
| 5,188,595 A | 2/1993 | Jacobi |
| 5,192,301 A | 3/1993 | Kamiya et al. |
| 5,207,656 A | 5/1993 | Kranys |
| 5,209,737 A | 5/1993 | Richartt |
| 5,211,370 A | 5/1993 | Powers |
| 5,211,633 A | 5/1993 | Strouder |
| 5,213,114 A | 5/1993 | Bailey, Jr. |
| 5,234,455 A | 8/1993 | Mulhollan |
| 5,242,409 A | 9/1993 | Buelna |
| 5,248,304 A | 9/1993 | Vigdorchik et al. |
| 5,263,922 A | 11/1993 | Sova et al. |
| 5,269,763 A | 12/1993 | Boehmer |
| D343,236 S | 1/1994 | Quigley et al. |
| 5,279,575 A | 1/1994 | Sugarbaker |
| D346,022 S | 4/1994 | Quigley et al. |
| 5,299,582 A | 4/1994 | Potts |
| 5,300,036 A | 4/1994 | Mueller |
| 5,308,336 A | 5/1994 | Hart et al. |
| 5,309,896 A | 5/1994 | Moll et al. |
| 5,316,541 A | 5/1994 | Fischer |
| 5,320,611 A | 6/1994 | Bonutti |
| 5,330,437 A | 7/1994 | Durman |
| 5,330,497 A | 7/1994 | Freitas |
| 5,336,192 A | 8/1994 | Palestrant |
| 5,342,385 A | 8/1994 | Norelli et al. |
| 5,350,364 A | 9/1994 | Stephens et al. |
| 5,364,345 A | 11/1994 | Lowery et al. |
| 5,366,478 A | 11/1994 | Brinkerhoff et al. |
| 5,368,545 A | 11/1994 | Schaller et al. |
| 5,383,861 A | 1/1995 | Hempel |
| 5,385,553 A | 1/1995 | Hart et al. |
| 5,391,156 A | 2/1995 | Hildwein et al. |
| 5,403,264 A | 4/1995 | Wohlers |
| 5,407,433 A | 4/1995 | Loomas |
| 5,423,848 A | 6/1995 | Washizuka et al. |
| 5,429,609 A | 7/1995 | Yoon |
| 5,431,676 A | 7/1995 | Durbal |
| 5,443,452 A | 8/1995 | Hart et al. |
| 5,456,284 A | 10/1995 | Ryan |
| 5,476,475 A | 12/1995 | Gadberry |
| 5,480,410 A | 1/1996 | Cuschieri et al. |
| 5,496,280 A | 3/1996 | Vandenbroeck |
| 5,503,112 A | 4/1996 | Luhman |
| 5,514,109 A | 5/1996 | Mollenauer et al. |
| 5,514,133 A | 5/1996 | Golub et al. |
| 5,520,632 A | 5/1996 | Leveen |

| | | | | | | |
|---|---|---|---|---|---|---|
| 5,522,791 | A | 6/1996 | Leyva | 6,162,206 A | 12/2000 | Bindokas |
| 5,522,824 | A | 6/1996 | Ashby | 6,163,949 A | 12/2000 | Neuenschwander |
| 5,524,644 | A | 6/1996 | Crook | 6,164,279 A | 12/2000 | Tweedle |
| 5,526,536 | A | 6/1996 | Cartmill | 6,171,282 B1 | 1/2001 | Ragsdale |
| 5,545,179 | A | 8/1996 | Williamson, IV | 6,183,486 B1 | 2/2001 | Snow et al. |
| 5,562,632 | A | 10/1996 | Davila | 6,238,373 B1 | 5/2001 | de la Torre et al. |
| 5,562,688 | A | 10/1996 | Riza | 6,254,533 B1 | 7/2001 | Fadem et al. |
| 5,584,850 | A | 12/1996 | Hart et al. | 6,254,534 B1 | 7/2001 | Butler et al. |
| 5,601,579 | A | 2/1997 | Semertzides | 6,258,065 B1 | 7/2001 | Dennis |
| 5,620,415 | A | 4/1997 | Lucey | 6,315,770 B1 | 11/2001 | de la Torre et al. |
| 5,632,979 | A | 5/1997 | Goldberg | 6,319,246 B1 | 11/2001 | de la Torre et al. |
| 5,634,911 | A | 6/1997 | Hermann et al. | 6,322,541 B2 | 11/2001 | West |
| 5,634,936 | A | 6/1997 | Linden | 6,346,074 B1 | 2/2002 | Roth |
| 5,634,937 | A | 6/1997 | Mollenauer et al. | 6,382,211 B1 | 5/2002 | Crook |
| 5,636,645 | A | 6/1997 | Ou | 6,420,475 B1 | 7/2002 | Chen |
| 5,640,977 | A | 6/1997 | Leahy et al. | 6,440,063 B1 | 8/2002 | Beane |
| 5,649,550 | A | 7/1997 | Crook | 6,450,983 B1 | 9/2002 | Rambo |
| 5,653,705 | A | 8/1997 | de la Torre et al. | 6,454,783 B1 | 9/2002 | Piskun |
| 5,657,963 | A | 8/1997 | Hinchliffe | 6,485,435 B1 | 11/2002 | Bakal |
| 5,658,272 | A | 8/1997 | Hasson | 6,533,734 B1 | 3/2003 | Corley, III et al. |
| 5,658,306 | A | 8/1997 | Kieturakis | 6,554,793 B1 | 4/2003 | Pauker |
| 5,672,168 | A | 9/1997 | de la Torre et al. | 6,578,577 B2 | 6/2003 | Bonadio et al. |
| 5,685,854 | A | 11/1997 | Green | 6,582,364 B2 | 6/2003 | Butler et al. |
| 5,707,703 | A | 1/1998 | Rothrum et al. | 6,589,167 B1 | 7/2003 | Shimonmura |
| 5,709,664 | A | 1/1998 | Vandenbroeck | 6,589,211 B1 | 7/2003 | MacLeod |
| 5,720,730 | A | 2/1998 | Blake, III | 6,607,504 B2 | 8/2003 | Haarala |
| 5,738,628 | A | 4/1998 | Sierocuk et al. | 6,613,952 B2 | 9/2003 | Rambo |
| 5,741,234 | A | 4/1998 | Aboul-Hosn | 6,623,426 B2 | 9/2003 | Bonadio et al. |
| 5,741,298 | A | 4/1998 | MacLeod | 6,706,050 B1 | 3/2004 | Giannadakis |
| 5,749,882 | A | 5/1998 | Hart et al. | 6,714,298 B2 | 3/2004 | Ryer |
| 5,755,660 | A | 5/1998 | Tyagi | 6,723,044 B2 | 4/2004 | Pulford |
| 5,769,783 | A | 6/1998 | Fowler | 6,796,940 B2 | 9/2004 | Bonadio et al. |
| 5,782,812 | A | 7/1998 | Hart et al. | 6,797,765 B2 | 9/2004 | Pearce |
| 5,795,290 | A | 8/1998 | Bridges | 6,814,078 B2 | 11/2004 | Crook |
| 5,803,919 | A | 9/1998 | Hart et al. | 6,814,700 B1 | 11/2004 | Mueller et al. |
| 5,803,921 | A | 9/1998 | Bonadio | 6,840,951 B2 | 1/2005 | de la Torre et al. |
| 5,807,350 | A | 9/1998 | Diaz | 6,846,287 B2 | 1/2005 | Bonadio et al. |
| 5,810,721 | A | 9/1998 | Mueller et al. | 6,866,861 B1 | 3/2005 | Luhman |
| 5,813,409 | A | 9/1998 | Leahy et al. | 6,884,253 B1 | 4/2005 | McFarlane |
| 5,814,026 | A | 9/1998 | Yoon | 6,902,541 B2 | 6/2005 | Zevex |
| 5,817,062 | A | 10/1998 | Flom | 6,908,430 B2 | 6/2005 | Caldwell |
| 5,820,555 | A | 10/1998 | Mueller | 6,916,331 B2 | 7/2005 | Mollenauer et al. |
| 5,832,925 | A | 11/1998 | Rothrum | 6,936,037 B2 | 8/2005 | Bubb |
| 5,853,395 | A | 12/1998 | Crook et al. | 6,939,296 B2 | 9/2005 | Ewers |
| 5,871,474 | A | 2/1999 | Hermann et al. | 6,945,932 B1 | 9/2005 | Caldwell et al. |
| 5,882,344 | A | 3/1999 | Strouder | 6,958,037 B2 | 10/2005 | Ewers |
| 5,899,208 | A | 5/1999 | Bonadio | 6,979,324 B2 | 12/2005 | Bybordi |
| 5,904,703 | A | 5/1999 | Beane | 7,008,377 B2 | 3/2006 | Beane |
| 5,906,577 | A | 5/1999 | Beane et al. | 7,052,454 B2 | 5/2006 | Taylor |
| 5,916,232 | A | 6/1999 | Hart | 7,081,089 B2 | 7/2006 | Bonadio et al. |
| 5,947,922 | A | 9/1999 | MacLeod | 7,195,590 B2 | 3/2007 | Butler et al. |
| 5,951,467 | A | 9/1999 | Picha et al. | 2001/0037053 A1 | 11/2001 | Bonadio et al. |
| 5,957,913 | A | 9/1999 | de la Torre et al. | 2001/0039430 A1 | 11/2001 | Dubrul et al. |
| 5,964,781 | A | 10/1999 | Mollenauer et al. | 2002/0038077 A1 | 3/2002 | de la Torre et al. |
| 5,993,485 | A | 11/1999 | Beckers | 2003/0139756 A1 | 7/2003 | Brustad |
| 5,994,450 | A | 11/1999 | Pearce | 2003/0187376 A1 | 10/2003 | Rambo |
| 5,997,515 | A | 12/1999 | de la Torre et al. | 2003/0192553 A1 | 10/2003 | Rambo |
| 6,024,736 | A | 2/2000 | de la Torre et al. | 2003/0225392 A1 | 12/2003 | McMichael |
| 6,025,067 | A | 2/2000 | Fay | 2004/0024363 A1 | 2/2004 | Goldberg |
| 6,033,426 | A | 3/2000 | Kaji | 2004/0049100 A1 | 3/2004 | Butler et al. |
| 6,033,428 | A | 3/2000 | Sardella | 2004/0073090 A1 | 4/2004 | Butler et al. |
| 6,042,573 | A | 3/2000 | Lucey | 2004/0092796 A1 | 5/2004 | Butler et al. |
| 6,048,309 | A | 4/2000 | Flom et al. | 2004/0093018 A1 | 5/2004 | Johnson |
| 6,059,816 | A | 5/2000 | Moenning | 2004/0106942 A1 | 6/2004 | Taylor |
| 6,077,288 | A | 6/2000 | Shimomura et al. | 2004/0143158 A1 | 7/2004 | Hart et al. |
| 6,110,154 | A | 8/2000 | Shimomura et al. | 2004/0215063 A1 | 10/2004 | Bonadio et al. |
| 6,123,689 | A | 9/2000 | To | 2005/0020884 A1 | 1/2005 | Heart et al. |
| 6,142,935 | A | 11/2000 | Flom et al. | 2005/0033246 A1 | 2/2005 | Ahlberg |
| 6,142,936 | A | 11/2000 | Beane et al. | 2005/0059865 A1 | 3/2005 | Kahle |
| 6,150,608 | A | 11/2000 | Wambeke | 2005/0065543 A1 | 3/2005 | Kahle |
| 6,159,182 | A | 12/2000 | Davis | 2005/0090713 A1 | 4/2005 | Gonzales et al. |
| 6,162,172 | A | 12/2000 | Cosgrove et al. | 2005/0090716 A1 | 4/2005 | Bonadio et al. |
| 6,162,196 | A | 12/2000 | Hart et al. | 2005/0090717 A1 | 4/2005 | Bonadio et al. |

| | | | | | |
|---|---|---|---|---|---|
| 2005/0131349 A1 | 6/2005 | Albrecht | WO | WO 86/06272 | 11/1986 |
| 2005/0148823 A1 | 7/2005 | Vaugh et al. | WO | WO 92/11880 | 7/1992 |
| 2005/0159647 A1 | 7/2005 | Hart et al. | WO | WO 92/21292 | 12/1992 |
| 2005/0192598 A1 | 9/2005 | Johnson | WO | WO 93/05740 | 4/1993 |
| 2005/0240082 A1 | 10/2005 | Bonadio et al. | WO | WO 95/05207 | 2/1995 |
| 2005/0241647 A1 | 11/2005 | Nguyen | WO | WO 95/07056 | 3/1995 |
| 2005/0277946 A1 | 12/2005 | Greenhalgh | WO | WO 95/22289 | 8/1995 |
| 2005/0288558 A1 | 12/2005 | Ewers | WO | WO 95/24864 | 9/1995 |
| 2005/0288634 A1 | 12/2005 | O'Herron | WO | WO 95/27445 | 10/1995 |
| 2006/0041270 A1 | 2/2006 | Lenker | WO | WO 95/27468 | 10/1995 |
| 2006/0047284 A1 | 3/2006 | Gresham | WO | WO 96/36283 | 11/1996 |
| 2006/0106402 A1 | 5/2006 | McLucas | WO | WO 97/32514 | 9/1997 |
| 2006/0149306 A1 | 7/2006 | Hart et al. | WO | WO 97/32515 | 9/1997 |
| 2006/0247498 A1 | 11/2006 | Bonadio et al. | WO | WO 98/35614 | 8/1998 |
| | | | WO | WO 98/48724 | 11/1998 |

FOREIGN PATENT DOCUMENTS

| | | | | | |
|---|---|---|---|---|---|
| DE | 37 37 121 | 5/1989 | WO | WO 99/03416 | 1/1999 |
| DE | 296 00 939 | 6/1998 | WO | WO 99/25268 | 5/1999 |
| EP | 0142262 | 5/1985 | WO | WO 99/29250 | 6/1999 |
| EP | 0537768 | 4/1993 | WO | WO 00/32116 | 6/2000 |
| EP | 0950376 | 10/1999 | WO | WO 00/32117 | 6/2000 |
| EP | 1118657 | 7/2001 | WO | WO 00/32119 | 6/2000 |
| FR | 1456623 | 9/1966 | WO | WO 00/32120 | 6/2000 |
| GB | 1151993 | 5/1969 | WO | WO 00/35356 | 6/2000 |
| GB | 1355611 | 6/1974 | WO | WO 00/54675 | 9/2000 |
| GB | 1372491 | 10/1974 | WO | WO 00/54676 | 9/2000 |
| GB | 1379772 | 1/1975 | WO | WO 00/54677 | 9/2000 |
| GB | 1400808 | 7/1975 | WO | WO 01/08563 | 2/2001 |
| GB | 1407023 | 9/1975 | WO | WO 01/08581 | 2/2001 |
| GB | 1496696 | 12/1977 | WO | WO 01/26558 | 4/2001 |
| GB | 2071502 | 9/1981 | WO | WO 01/91652 | 12/2001 |
| GB | 2255019 | 10/1992 | WO | WO 02/34108 A2 | 5/2002 |
| GB | 2275420 | 8/1994 | WO | WO 03/026512 A1 | 4/2003 |
| JP | 10-108868 | 4/1998 | WO | WO 03/034908 A3 | 5/2003 |
| JP | 11-290327 | 10/1999 | WO | WO 03/061480 A1 | 7/2003 |
| JP | 2001-61850 | 3/2001 | WO | WO 03/103548 A1 | 12/2003 |
| JP | 2004-195037 | 7/2004 | WO | WO 2004/026153 A1 | 4/2004 |
| RU | SU 1342485 | 1/1997 | WO | WO 2004/030547 A | 4/2004 |
| | | | WO | WO 2005/009257 A2 | 2/2005 |

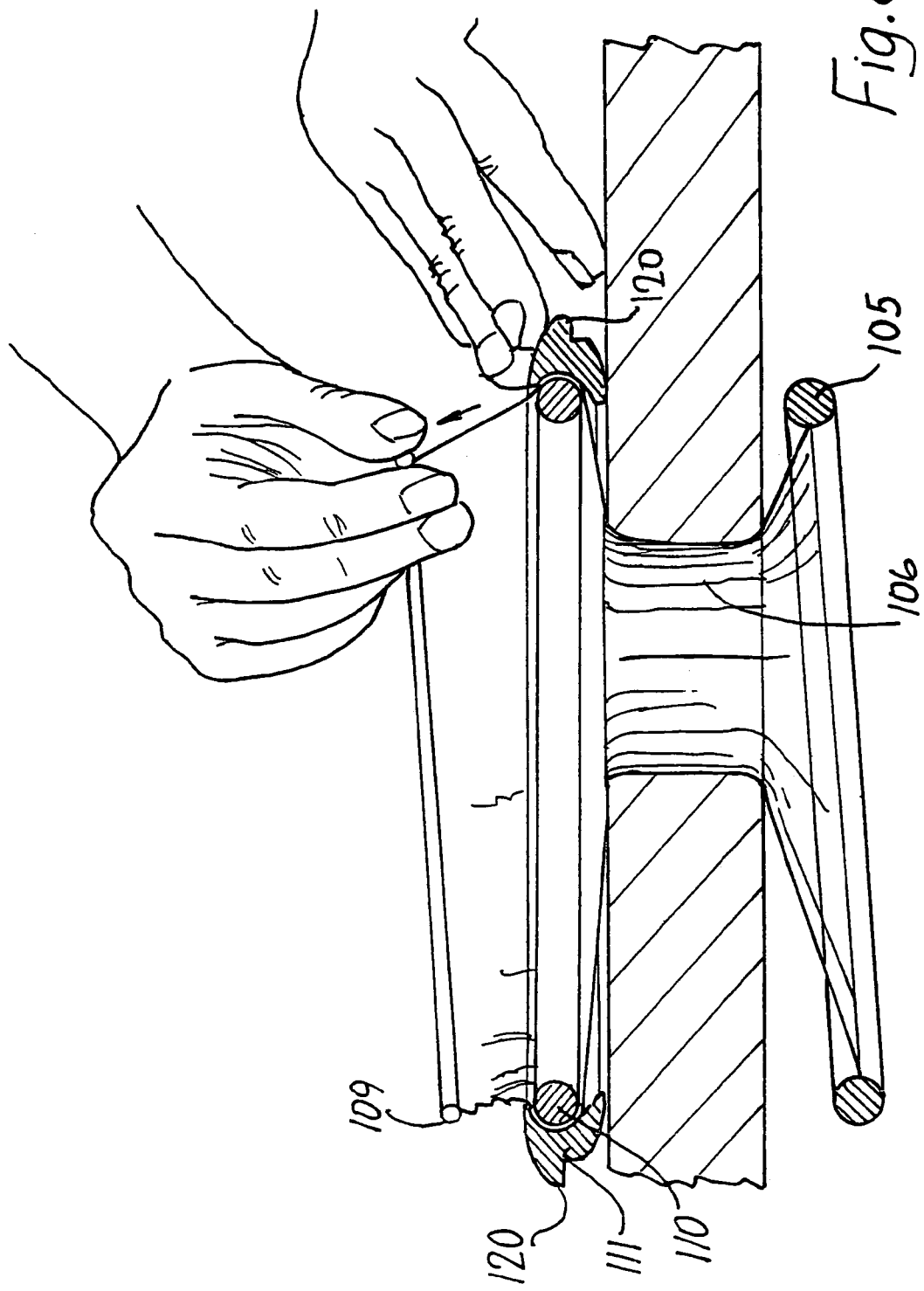

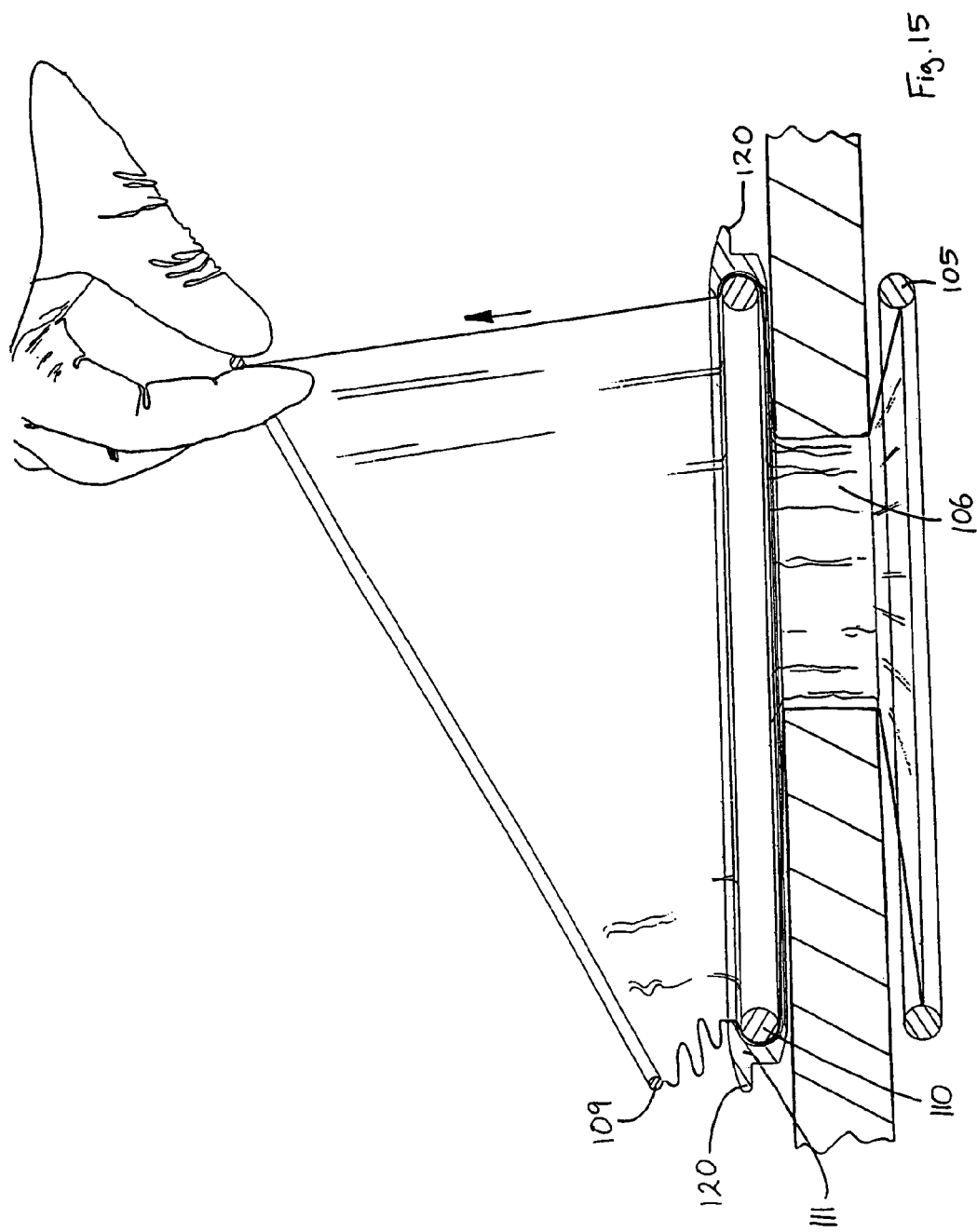

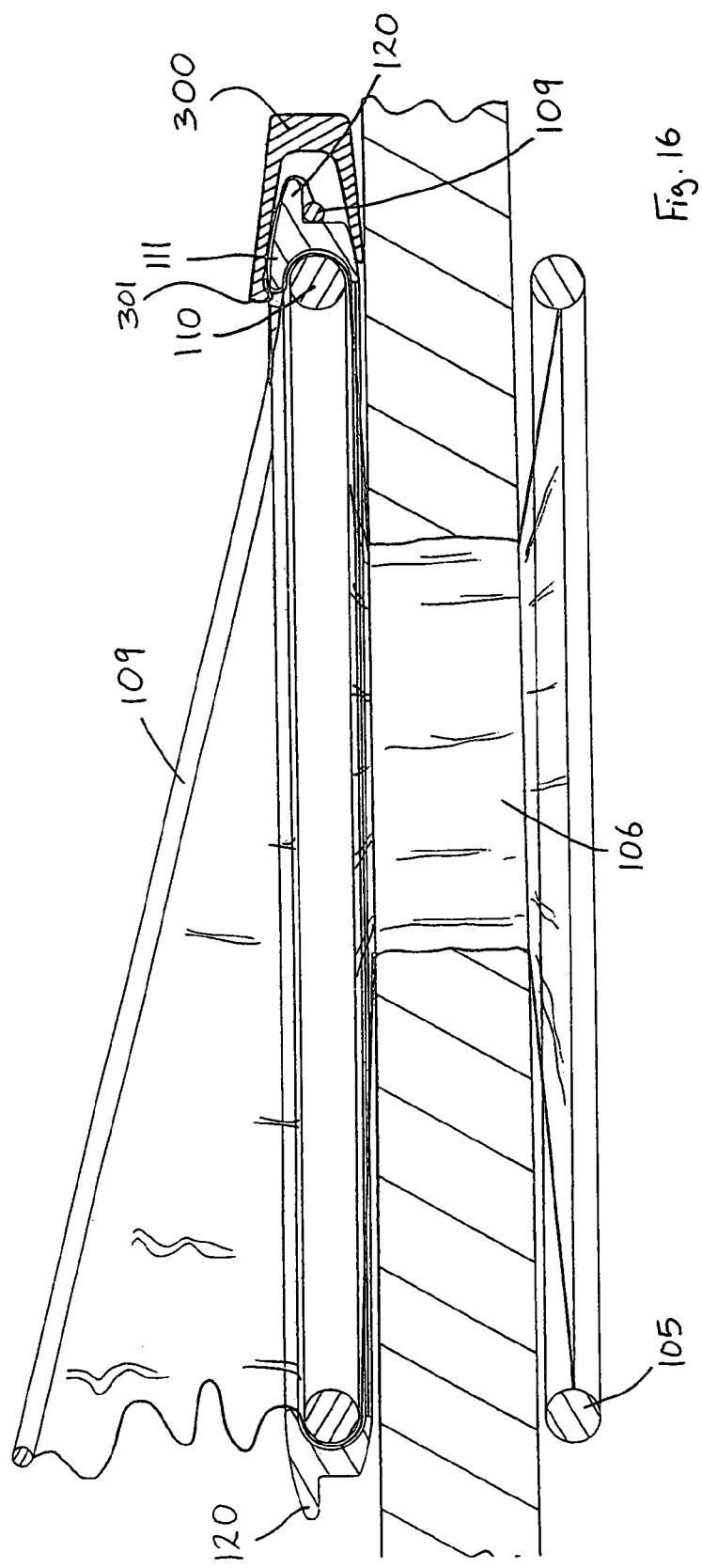

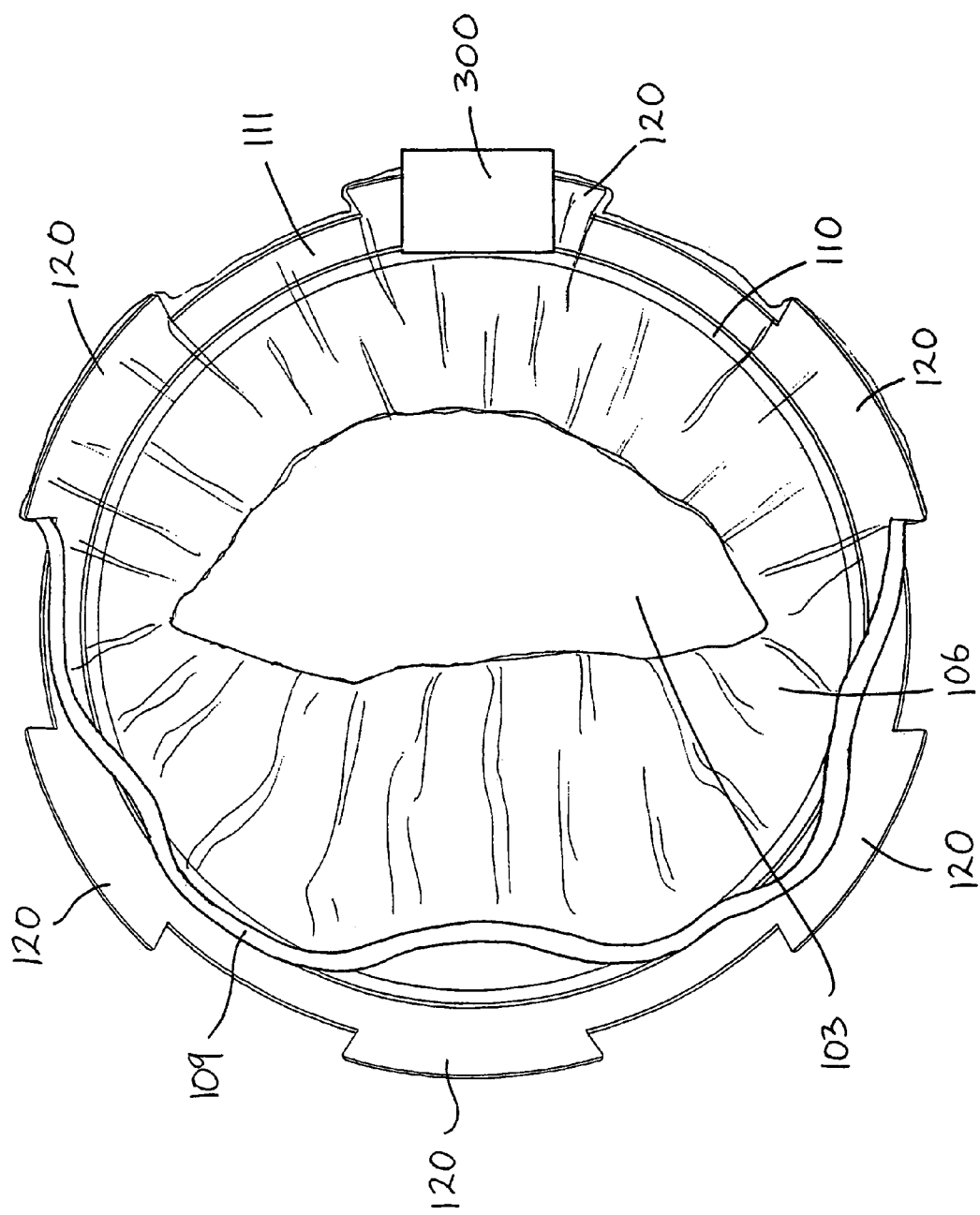

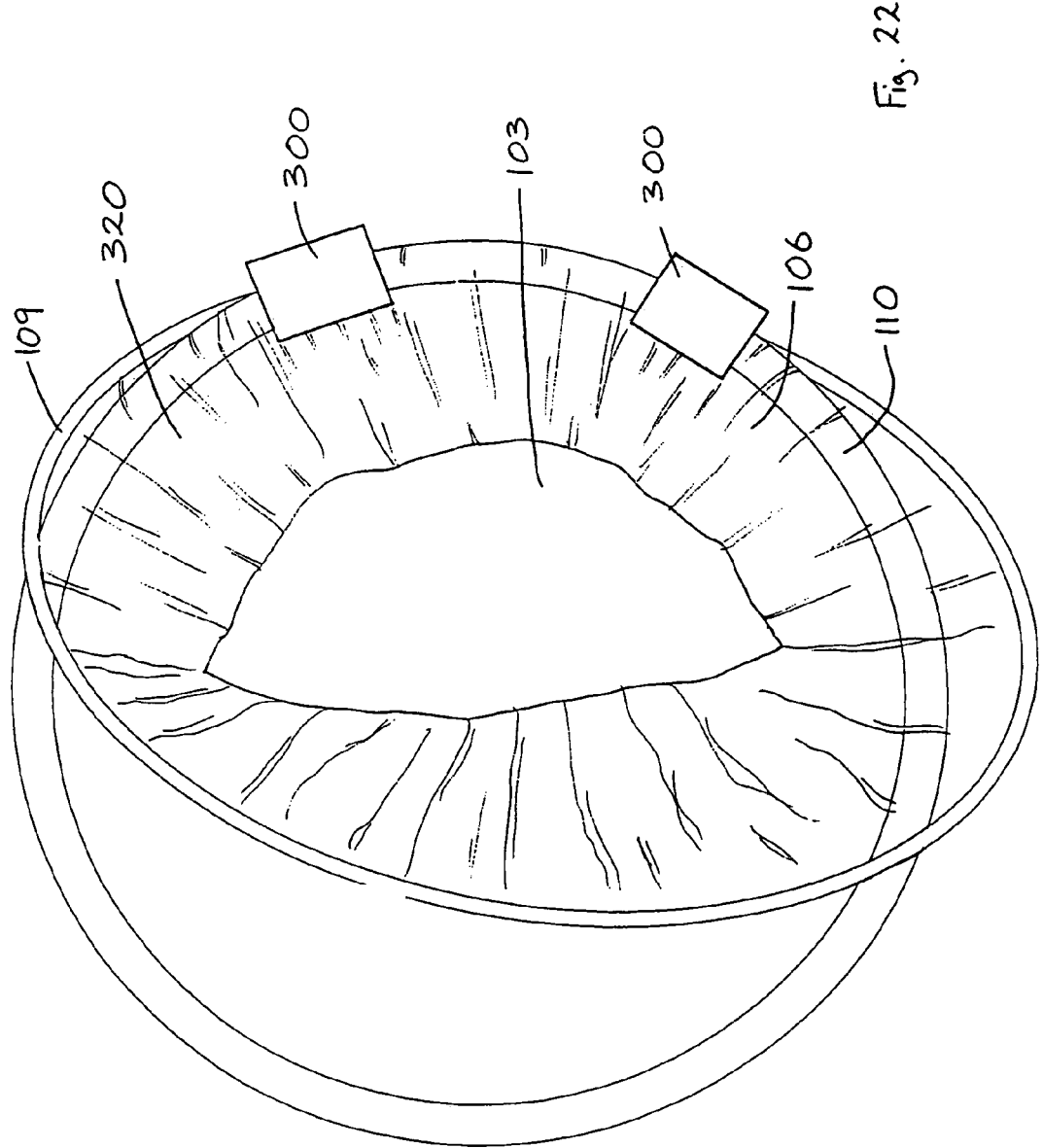

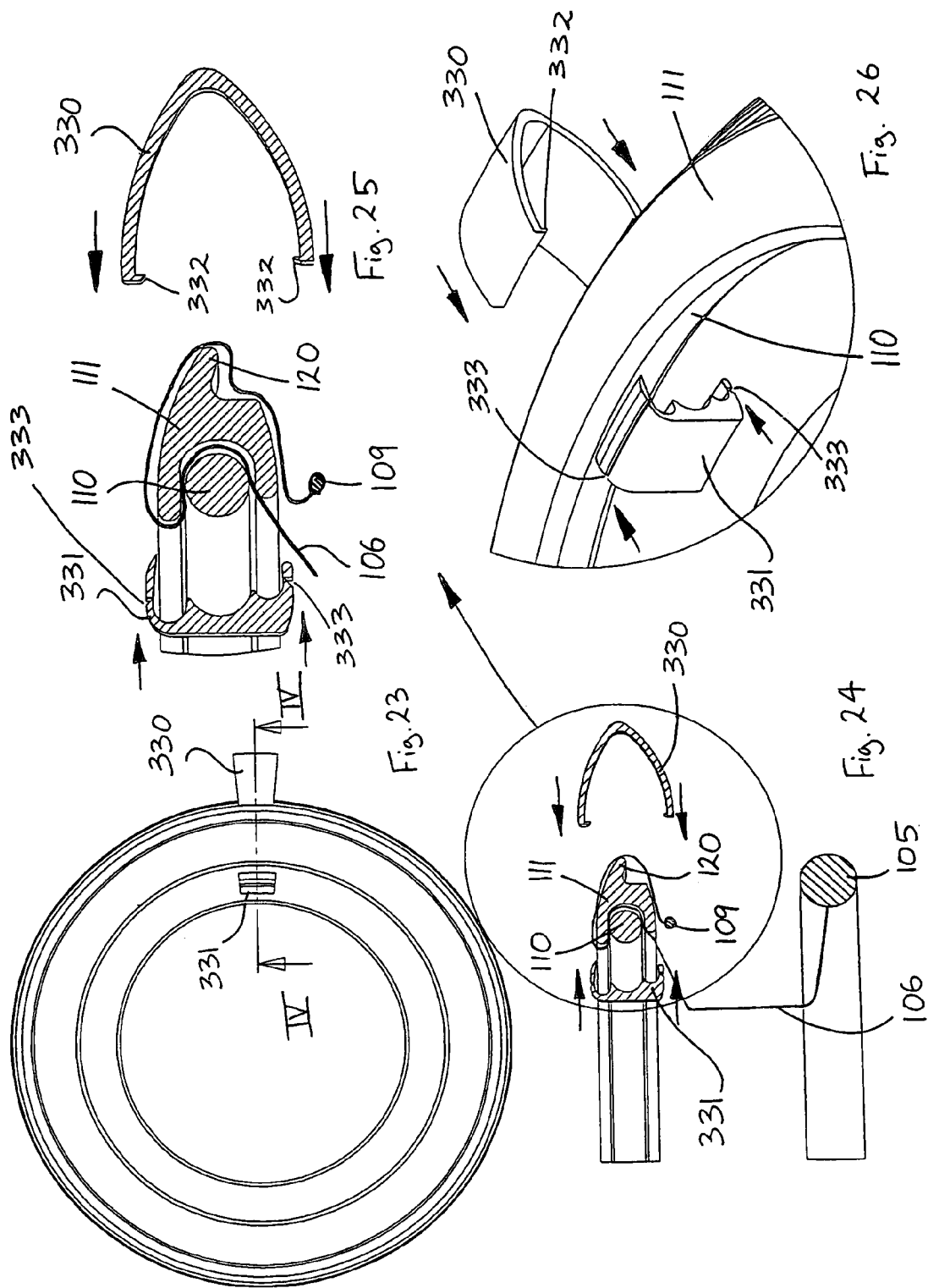

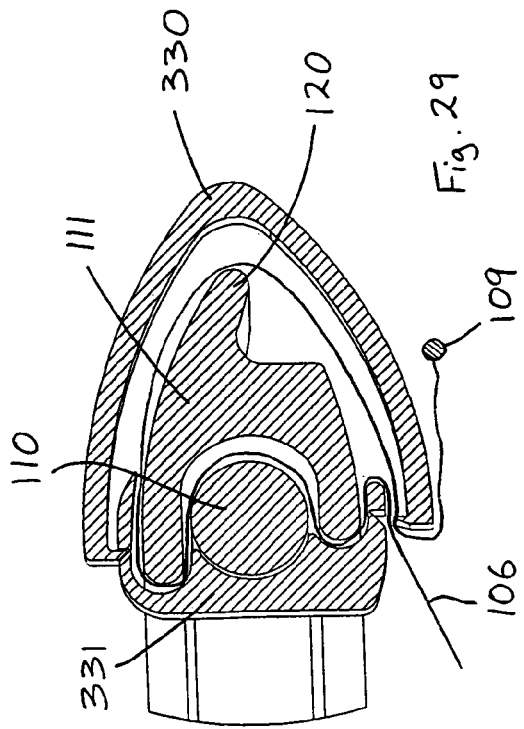
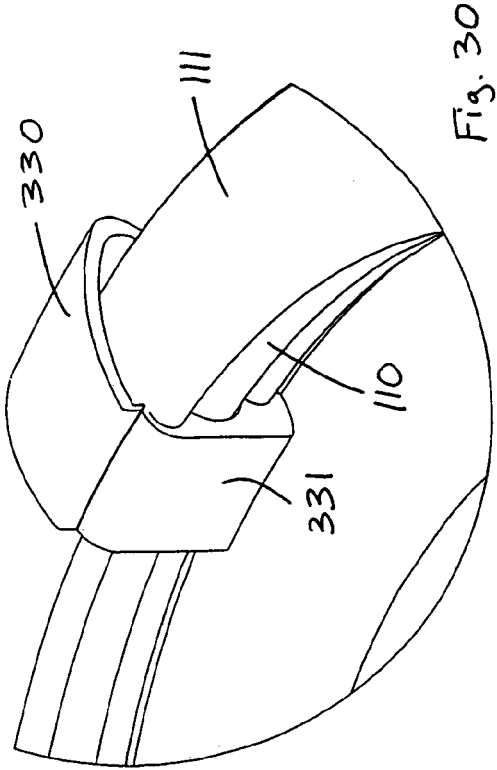
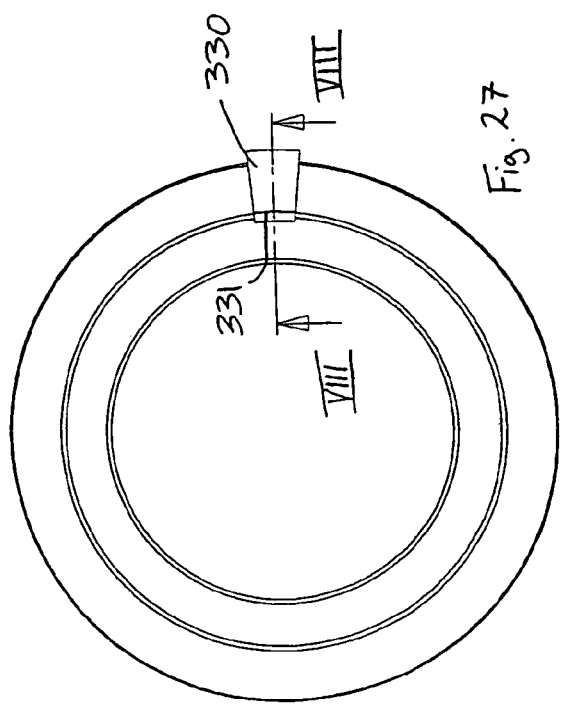
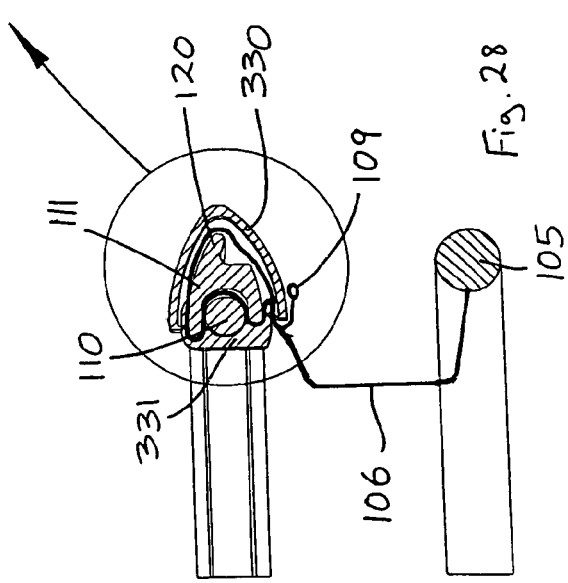

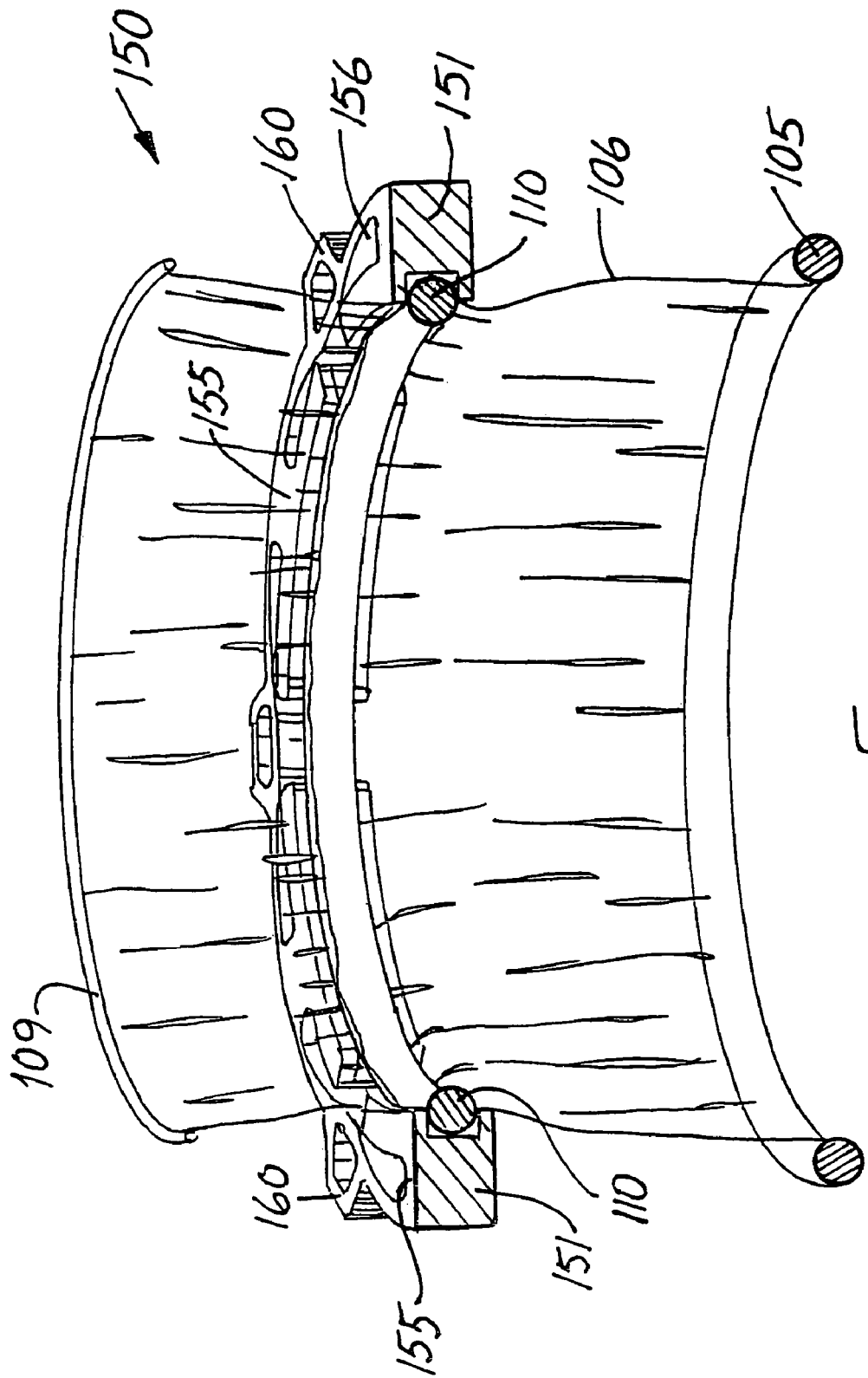

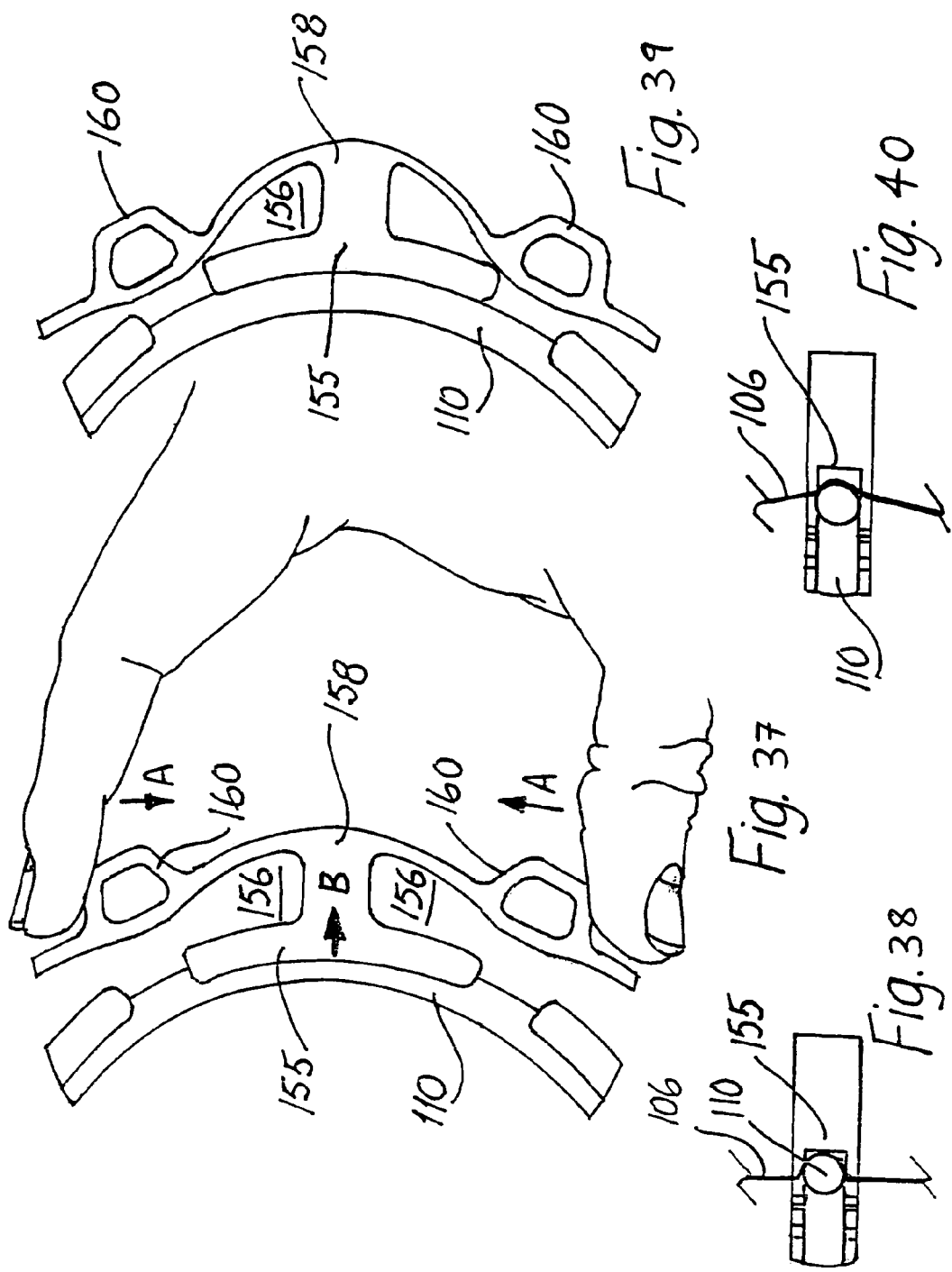

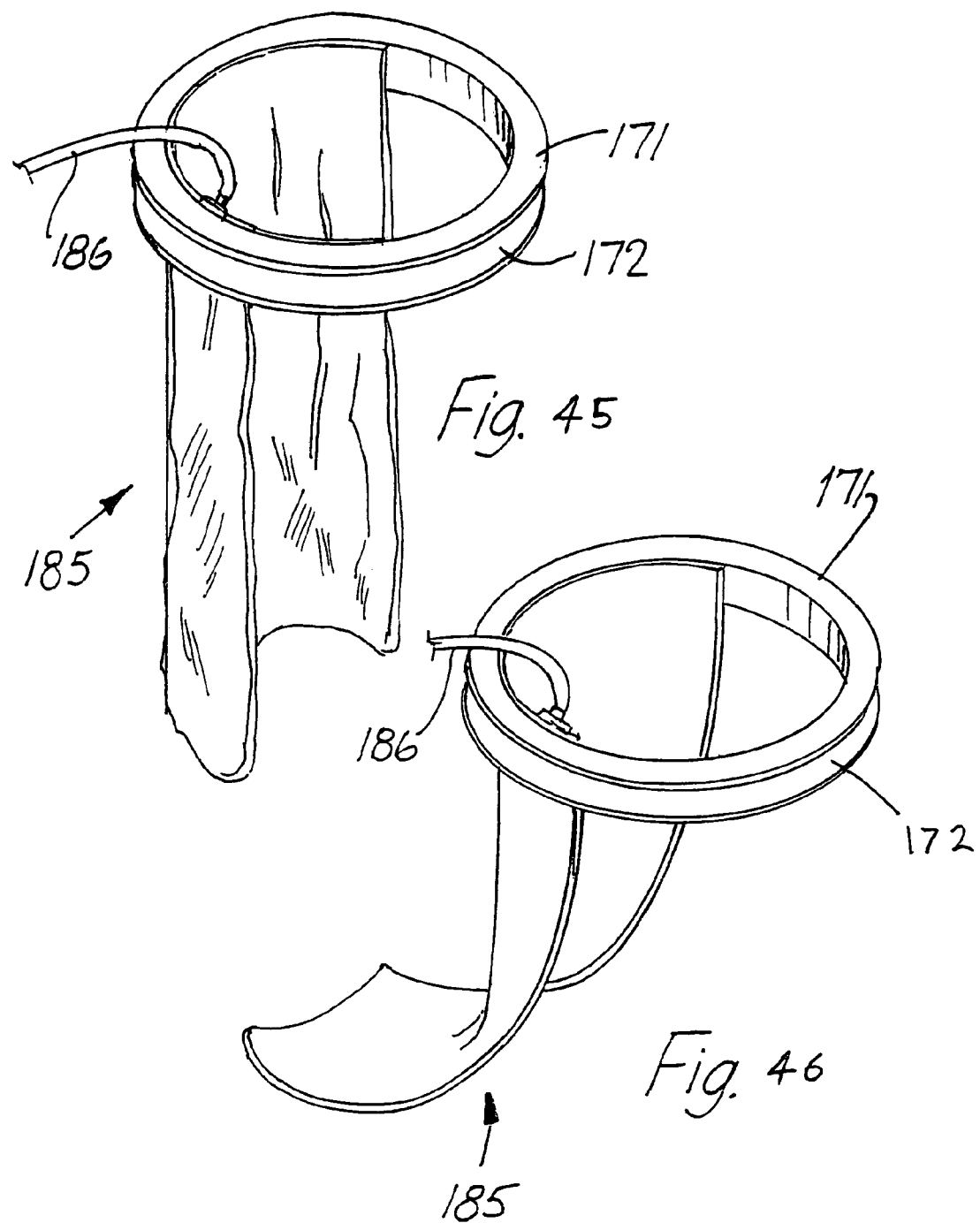

WOUND RETRACTOR

This application is a Continuation-In-Part of U.S. application Ser. No. 10/374,523, filed on Feb. 27, 2003 now U.S. Pat. No. 7,445,597 which is a Continuation of application Ser. No. 09/849,341, filed on May 7, 2001, now U.S. Pat. No. 6,582,364, which is a Continuation of application Ser. No. 09/688,138, filed Oct. 16, 2000, now U.S. Pat. No. 6,254,534, all of which are incorporated herein by reference. This application claims the priority to Ireland application No. 990861, filed on Oct. 14, 1999, Ireland application No. 991053, filed on Dec. 16, 1999, European application No. 00650010, filed on Feb. 18, 2000, and also claims the benefit of U.S. Provisional Application No. 60/401,023, filed on Aug. 6, 2002, all of which are incorporated herein by reference.

INTRODUCTION

The invention relates to a retractor. In particular the invention relates to a retractor for retracting the margins of an incision or a natural bodily orifice to provide maximum exposure of an organ or body structures for examination and/or access for surgical procedures, while also providing protection for the exposed sides of the incised tissue.

Various retractors are known. However in general known retractors are difficult and cumbersome to use, and/or are relatively expensive. In addition known retractors are limited to use with a particular size of incision and a particular patient anatomy.

This invention is directed towards providing an improved wound retractor which will overcome at least some of these problems, and in addition provide a means of wound protection during a surgical procedure.

STATEMENTS OF INVENTION

According to the invention there is provided a surgical wound retractor comprising:
a retracting member for insertion into a wound opening;
a proximal member for location externally of a wound opening; and
a clamp for clamping the retracting member to the proximal member.

In one embodiment of the invention the proximal member is movable relative to the retracting member to shorten the axial extent of the retracting member for lateral retraction of a wound opening.

The clamp may be configured to clamp the retracting member to a proximal surface of the proximal member. The clamp may be configured to clamp the retracting member to a distal surface of the proximal member.

In one case the clamp comprises at least one clip. Preferably the clamp comprises two or more clips spaced around the proximal member. Ideally the clips are equi-spaced around the proximal member. The location of the clip on the proximal member may be adjustable.

In a preferred embodiment the proximal member comprises at least one protrusion, and the clip is configured to clamp the retracting member to the proximal member at the protrusion. Ideally the clip is configured to clamp the retracting member from the outer side of the proximal member.

The clip may be substantially "C"-shaped. Ideally the clip is a bulldog clip.

In another case the clip comprises a first clip part and a second clip part. The first clip part is preferably an outer clip part and the second clip part is preferably an inner clip part. The first clip part may be configured to overlap the second clip part to enclose a portion of the proximal member. The clip may be configured for assembly of the first clip part and the second clip part together. Ideally the clip is configured for snap-fit assembly of the first clip part and the second clip part together.

In one embodiment the proximal member comprises an annular ring means. Preferably the annular ring means comprises a ring over which the retracting member may be led.

In another preferred case the annular ring means comprises an inner ring and an outer ring between which the retracting member may be led. Ideally the inner ring defines a projection for location in a complementary recess of the outer ring with the retracting member located therebetween.

The inner ring may be a relatively loose fit in the recess of the outer ring. The inner ring mat be a relatively tight fit in the recess of the outer ring to grip the retracting member therebetween.

In another embodiment at least portion of one of the rings is movable from a rest position in which the retracting member is substantially clamped between the rings to a release position in which at least portion of the retracting member is movable relative to the rings. In one case only portion of the retracting member is movable relative to the rings in the release position.

The outer ring may comprise a plurality of interconnected segments which are independently movable to facilitate localised release of the retracting member for adjusting the retraction force applied at a wound opening. Preferably the ring or segment thereof is manually manipulable between the clamped rest position and the release position.

In a further embodiment of the invention the proximal member comprises one or more anchor formations to which the retracting member may be attached on retraction of a wound opening.

A surface of the proximal member which engages with the retracting member may be of a material with a low coefficient of friction. Preferably the surface is of polytetrafluoroethylene.

An inner wound engaging portion of the retracting member preferably comprises a sleeve for lining a wound opening. Ideally a proximal portion of the retracting member comprises a sleeve extension of the inner wound engaging portion of the retracting member. Most preferably the sleeve is generally cylindrical.

Desirably the retracting member comprises a proximal reinforcing means. The proximal reinforcing means may comprise a ring.

In a further preferred case the retractor comprises a distal member coupled to a distal end of the retracting member for insertion into a wound opening. Ideally the distal member is of a resilient material. Most preferably the distal member comprises an O-ring.

The retractor may comprise a platform for attachment of another device to the retractor. In one case the platform is provided by the proximal member. In another case the platform is provided by the clamp.

In another aspect the invention provides a surgical wound retractor comprising:
a retracting member movable from an insertion configuration to a retracting configuration to retract laterally a wound opening; and
means for clamping the retracting member in the retracting configuration to maintain a wound opening retracted.

In a preferred embodiment the means for clamping comprises a clamp for clamping the retracting member to a proximal member located externally of the wound opening.

The invention also provides in a further aspect a surgical wound retractor comprising:

a distal anchoring member for insertion into a wound opening;

a connecting means having an inner wound engaging portion and an outer portion, the wound engaging portion being mounted to the distal anchoring member, the connecting means having an insertion configuration in which the inner wound engaging portion has a reduced radial dimension and a retracting configuration;

an external guide means for the outer portion of the connecting means;

the external guide means being movable relative to the connecting means to shorten the axial extent of the connecting means and thereby bias the wound engaging portion of the connecting means into the retracting configuration to retract the wound opening laterally; and a clamp for clamping the connecting means to the external guide means to maintain retraction of the opening.

According to another aspect of the invention there is provided a method of retracting a wound opening, the method comprising the steps of:

inserting a retracting member into a wound opening;

locating a proximal member externally of the wound opening;

moving at least part of the retracting member laterally to retract the wound opening; and clamping the retracting member to the proximal member to maintain the wound opening retracted.

In one embodiment of the invention the retracting member is clamped to the proximal member at one or more locations around the proximal member.

The method may comprise the step of adjusting the location of clamping of the retracting member to the proximal member.

In one case at least part of the retracting member is moved laterally by moving the proximal member relative to the retracting member to shorten the axial extent of the retracting member. Ideally the proximal member is moved relative to the retracting member by gripping the retracting member and pulling the retracting member relative to the proximal member.

In a further aspect of the invention, there is provided a method for retracting a wound opening using a surgical wound retractor comprising a distal anchoring member, a connecting means having a wound engaging portion mounted to the distal anchoring member and an outer portion, an external guide means for the outer portion of the connecting means and a clamp; the method comprising the steps of:

positioning the distal anchoring member to be retained inside a wound opening with the connecting means extending outwardly therefrom through the opening;

moving the external guide means relative to the outer portion of the connecting means to shorten the axial extent of the connecting means and thereby bias the wound engaging portion into a retracting configuration to retract the wound opening; and clamping the connecting means to the external anchoring means to maintain retraction of the wound opening.

BRIEF DESCRIPTION OF THE DRAWINGS

The invention will be more clearly understood from the following description thereof given by way of example only with reference to the accompanying drawings, in which:

FIG. 15 is a cross-sectional, side view illustrating lateral retraction of a wound opening using the retractor of FIG. 2;

FIG. 16 is a cross-sectional, side view of the clip of FIG. 14 mounted to the retractor of FIG. 15;

FIG. 17 is a plan view of the clip of FIG. 14 mounted to the retractor of FIG. 15;

FIG. 22 is a plan view illustrating retraction of a wound opening using the retractor of FIGS. 20 and 21 and two of the clips of FIG. 14;

FIG. 23 is a plan view of the retractor of FIG. 2 and another clip according to the invention;

FIG. 24 is a view along line IV-IV in FIG. 23;

FIG. 25 is an enlarged, cross-sectional, side view of the retractor of FIG. 2 and the clip of FIG. 23;

FIG. 26 is a perspective view of the retractor of FIG. 2 and the clip of FIG. 23;

FIGS. 27 to 30 are views similar to FIGS. 23 to 26 of the clip of FIG. 23 mounted to the retractor of FIG. 2;

FIGS. 35 and 36 are perspective cut-away views of the retractor of FIG. 34 in different positions;

FIG. 37 is a schematic plan view illustrating manipulation of a part of the retractor of FIGS. 34 to 36;

FIG. 38 is a side cross sectional view of the retractor part in the configuration of FIG. 37;

FIG. 39 is a schematic plan view of the retractor part in a release position;

FIG. 40 is a side cross sectional view of the retractor part in the configuration of FIG. 39;

FIG. 45 is a perspective view of a form retaining device in a pliable state for use with a wound retractor according to the invention;

FIG. 46 is a perspective view of the form retaining device of FIG. 45 in a stiff state;

DETAILED DESCRIPTION

Figure 3:
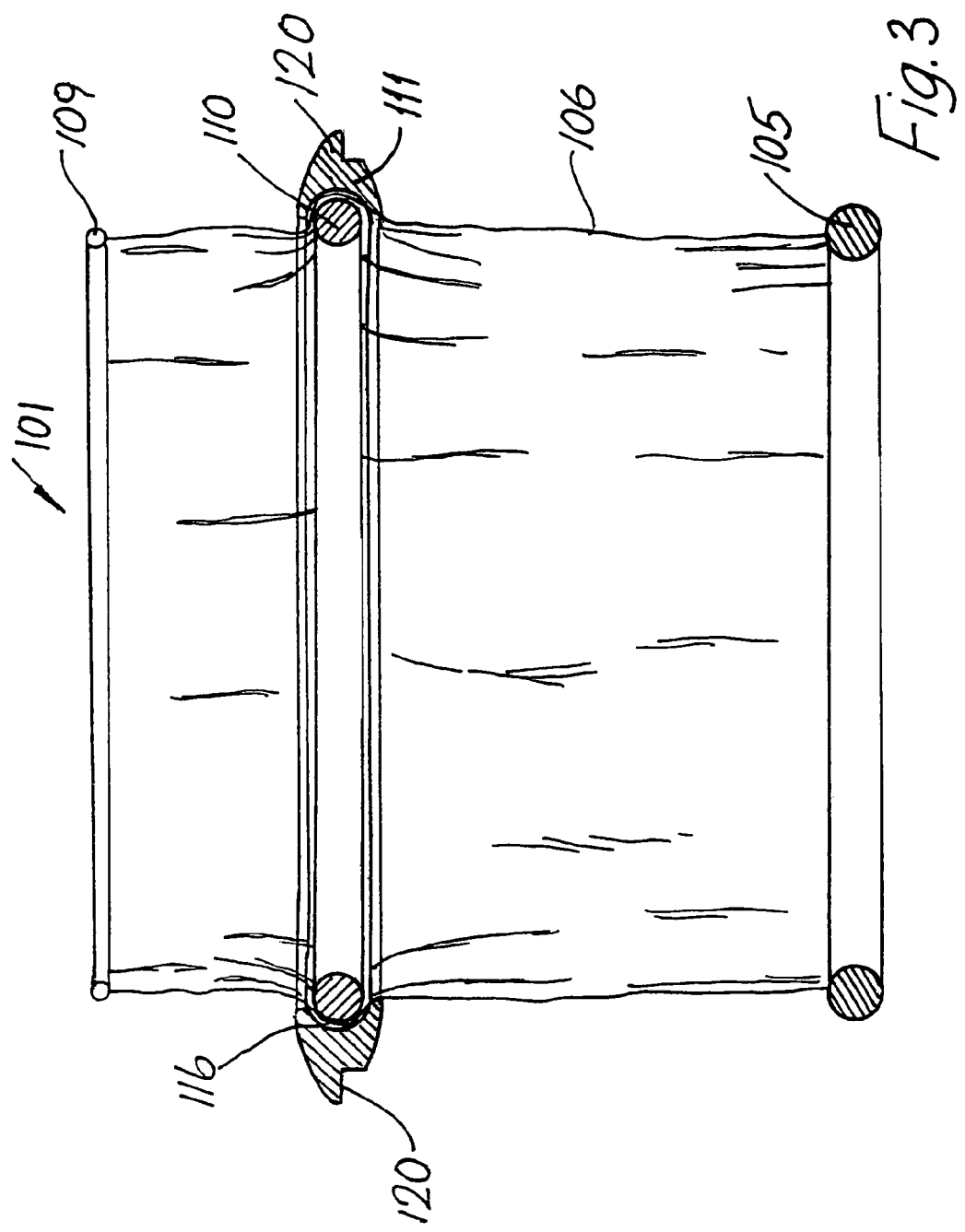
FIG. 3 is a side cross sectional view of the assembled retractor of FIG. 2.
Figure 4:
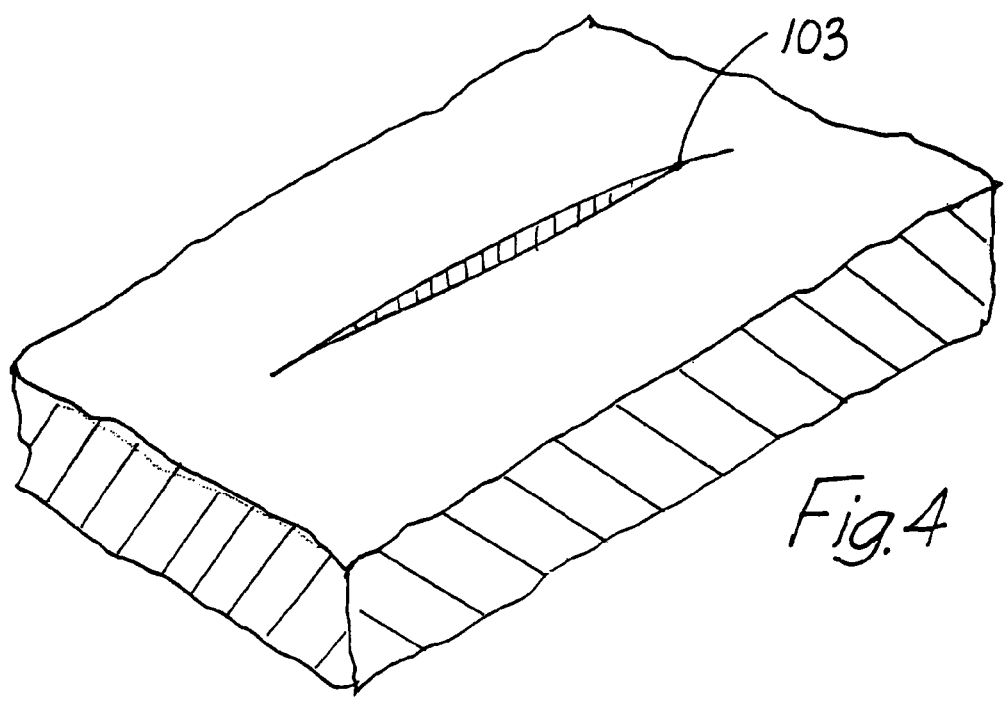
FIG. 4 is a perspective view of an unretracted wound opening.

Referring to FIGS. 1 to 13 there is illustrated a wound retractor 101 according to the invention, which in the case illustrated is used to retract the margins of a wound such as an abdominal wound opening 103, as illustrated in FIG. 4.

The retractor 101 comprises a distal anchoring member, in this case in the form of a resilient inner O-ring 105, for insertion into the wound opening 103, and a connecting means, in this case in the form of an elastomeric sleeve 106 which is substantially cylindrical. The sleeve 106 has an inner wound engaging portion and an outer portion, and the wound engaging portion is attached to the inner O-ring 105. The sleeve 106 has an insertion configuration in which the inner wound engaging portion has a reduced radial dimension and a retracting configuration to retract the wound opening 103 laterally.

An external guide means is provided for the outer portion of the sleeve 106, and in this case the guide means comprises an inner ring part 110 and an outer ring part 111 between which the sleeve 106 is led. The retractor 101 includes external anchoring means for anchoring the sleeve 106 to maintain retraction of the wound opening 103, and in this case the anchoring means is provided by a plurality of anchor formations 120 on the outer surface of the outer ring part 111 (FIG. 2), the formations 120 extending radially outwardly to define hooks.

The outer ring part 111 is of the same annular shape as the inner ring part 110 but has a larger diameter and a recess 116. The inner ring part 110 is of a relatively stiff material and mates with the outer ring part 111 in the recess 116 to slidably retain the sleeve 106 therebetween, as illustrated in FIG. 3. In this case the ring parts 110, 111 are a relatively loose fit to facilitate movement of the ring parts 110, 111 relative to the sleeve 106 to shorten the axial extent of the sleeve 106 and thereby bias the wound engaging portion into the retracting configuration to retract the wound opening 103 laterally.

The ring parts 110, 111 are of a material with a low coefficient of friction such as Polytetrafluoroethylene (PTFE). PTFE is a tough, non-resilient material of moderate tensile strength and with excellent lubricity.

Figure 1:
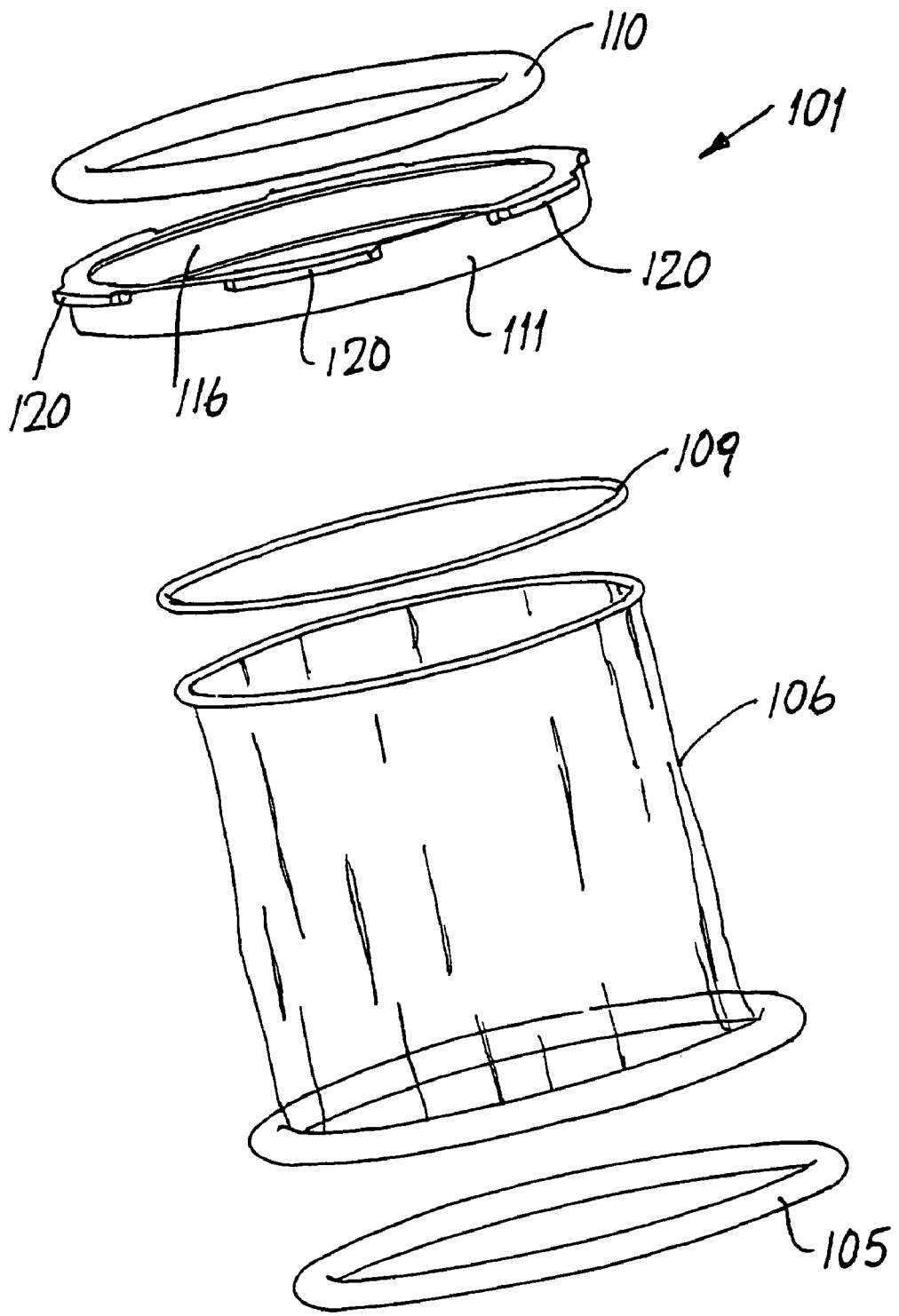
FIG. 1 is an exploded view of a wound retractor according to the invention.
Figure 2:
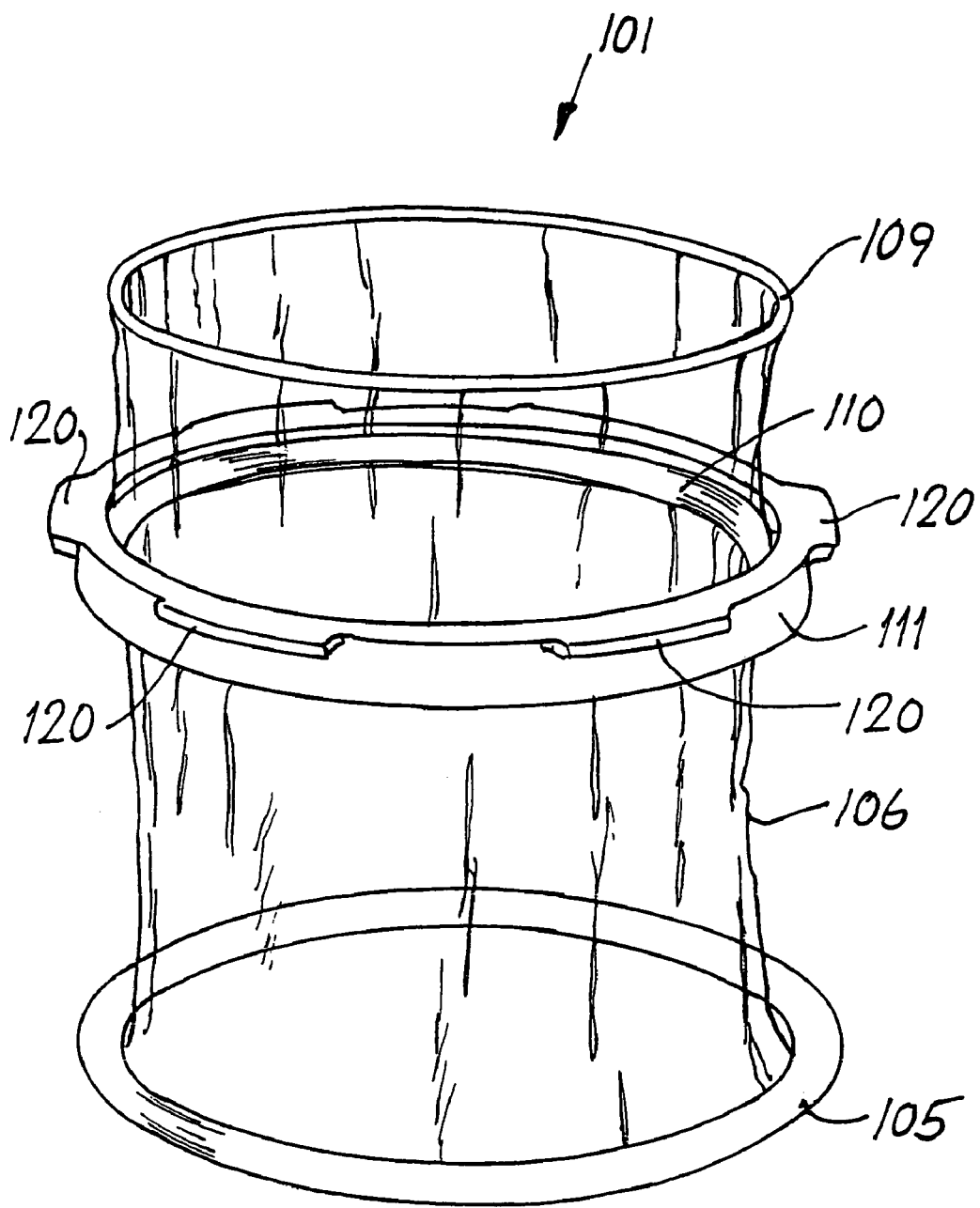
FIG. 2 is a perspective view of the retractor of FIG. 1 assembled.

The retractor 101 also includes a proximal reinforcing means for engagement with the anchor formations 120, and in this case the reinforcing means is provided by a resilient outer O-ring 109 of a material which is flexible relative to the inner O-ring 105. The outer O-ring 109 is attached to the proximal end of the sleeve 106, the rings 105, 109 helping to maintain the open shape of the sleeve 106 at its extremities (FIG. 2).

Figure 5:
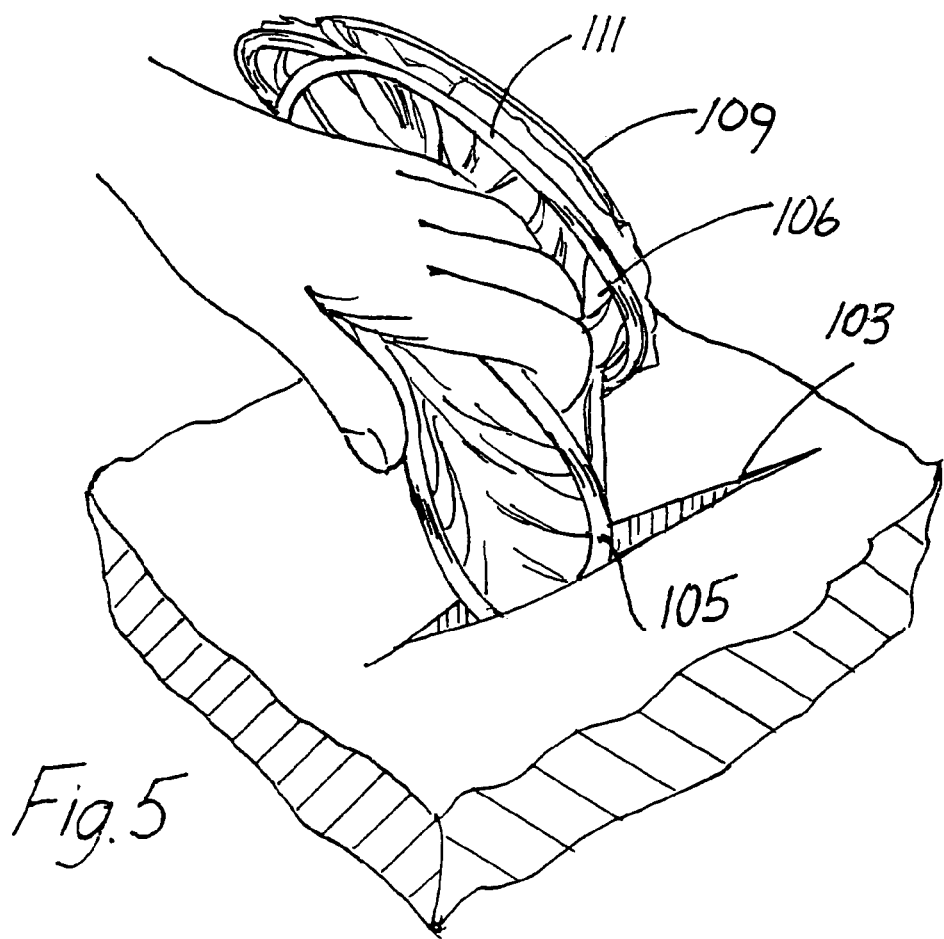
FIG. 5 is a perspective view illustrating insertion of part of the retractor of FIG. 2 into the wound opening.
Figure 6:
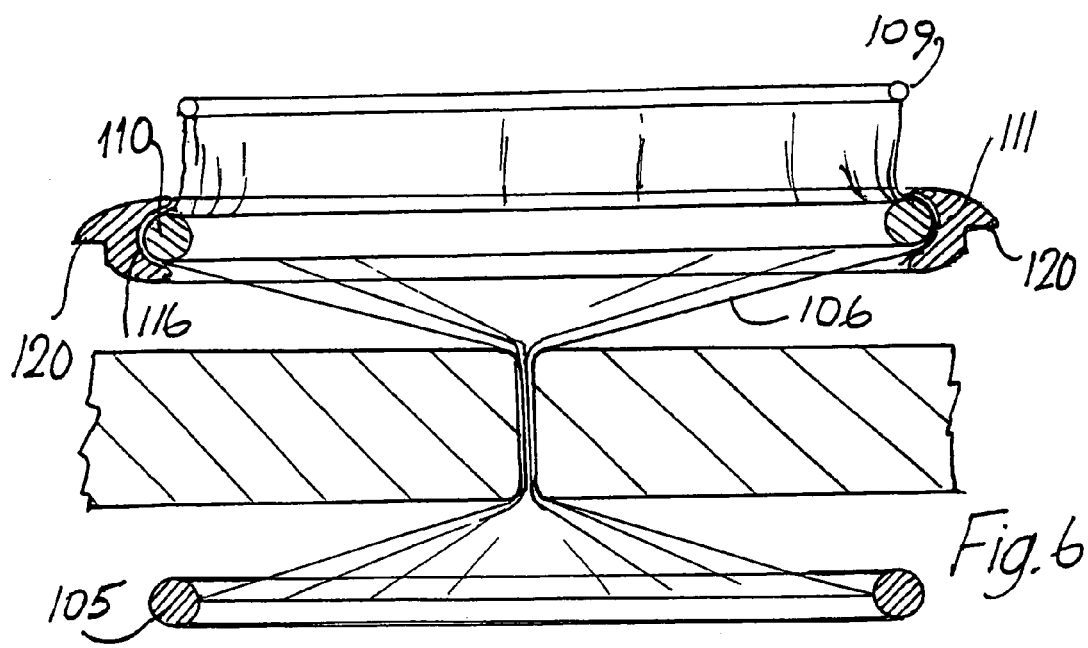
FIG. 6 is a side cross sectional view of the retractor of FIG. 2 after insertion.
Figure 7:
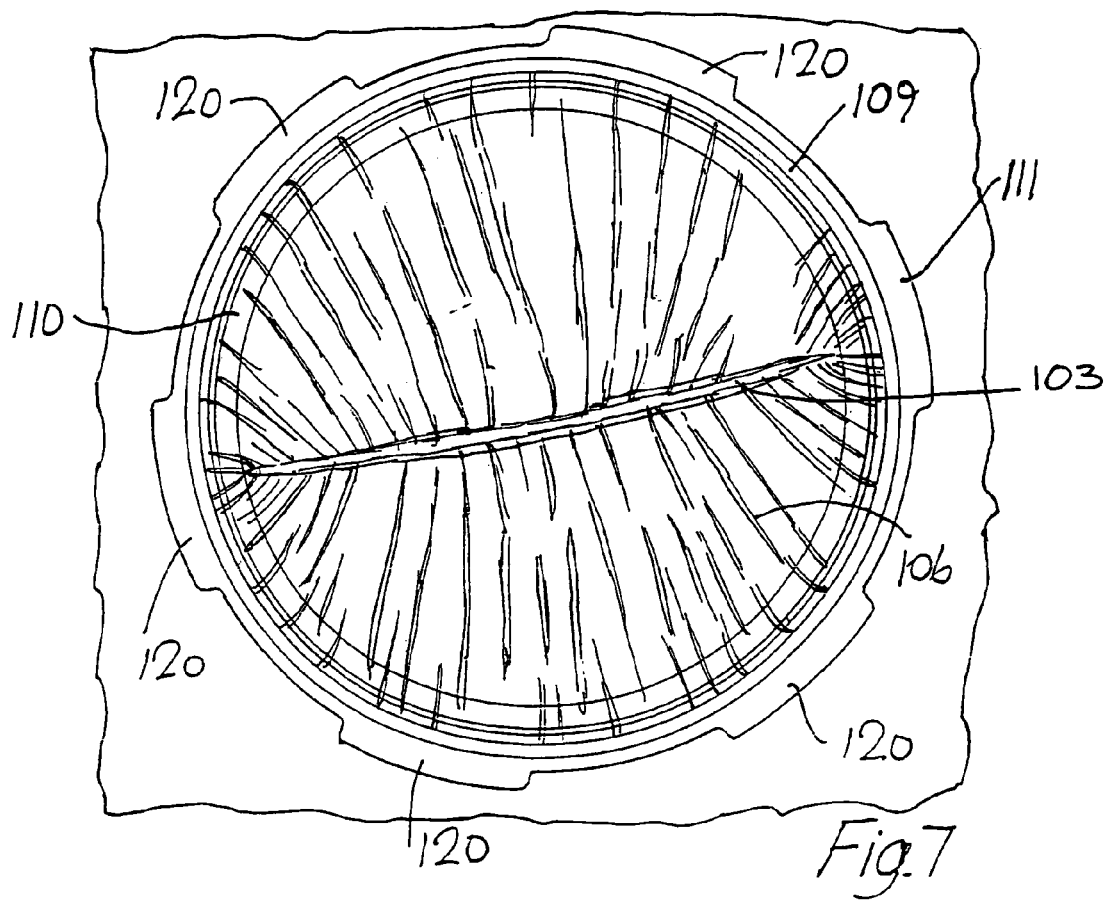
FIG. 7 is a plan view of the retractor of FIG. 2 after insertion.
Figure 8B:
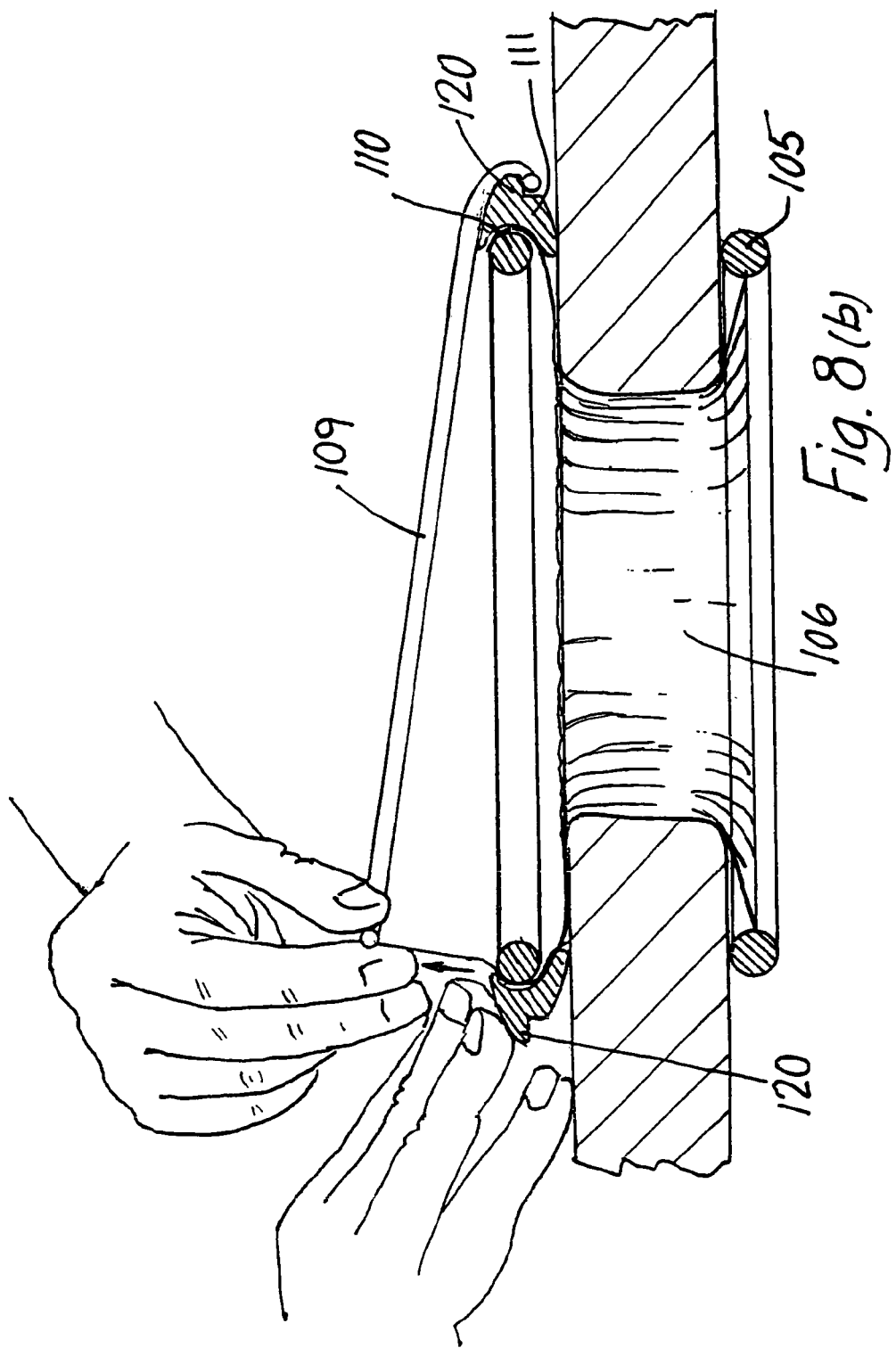
FIGS. 8(*a*) and 8(*b*) are side cross sectional views illustrating lateral retraction of the wound opening using the retractor of FIG. 2.

In use the inner O-ring 105 and the sleeve 106 are squeezed into the insertion configuration for insertion of the inner O-ring 105 into the wound opening 103 (FIG. 5). The inner O-ring 105 is of a polymeric material which facilitates scrunching up of the inner O-ring 105 into a low-profile, elongate shape, as illustrated in FIG. 5, to facilitate ease of use. On release of the inner O-ring 105, the resilient O-ring 105 returns to its normal O-shape overlapping an inner edge of the wound opening 103 to safely anchor the retractor 101 in the wound, as illustrated in FIG. 6. As may be seen from FIGS. 6 and 7, after insertion of the inner O-ring 105, the wound opening 103 is substantially closed and the sleeve 106 is in a wrinkled compressed configuration.

Figure 9:
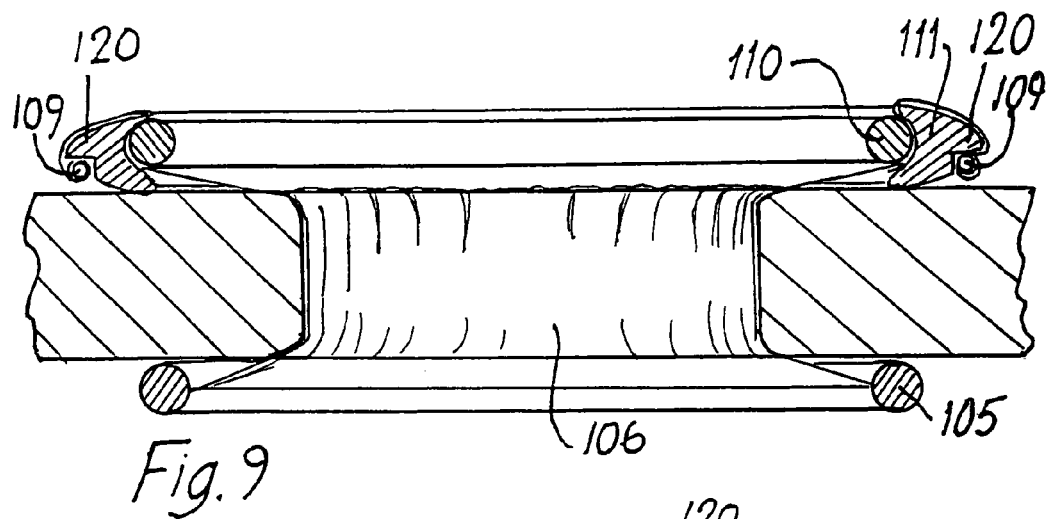
FIG. 9 is a side cross sectional view of the retractor of FIG. 2 after lateral retraction of the wound opening.
Figure 10:
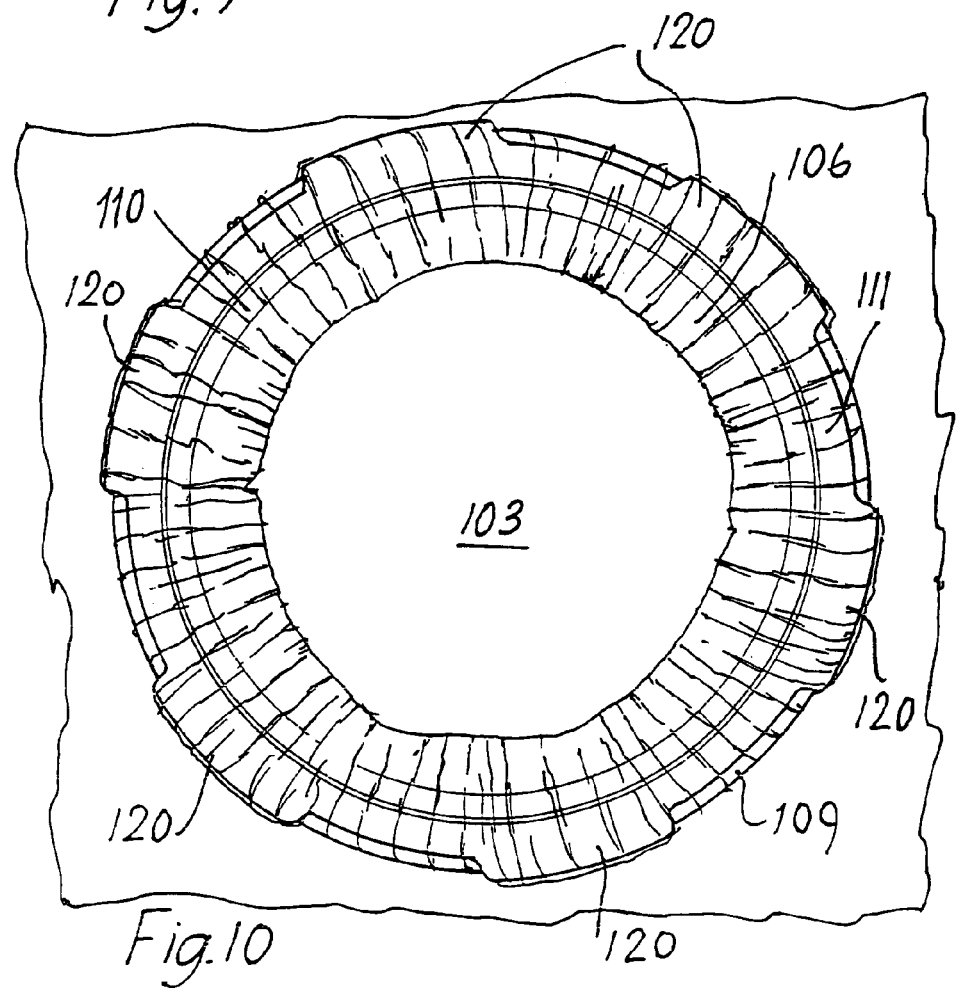
FIG. 10 is a plan view of the retractor of FIG. 2 after lateral retraction of the wound opening.
Figure 11:
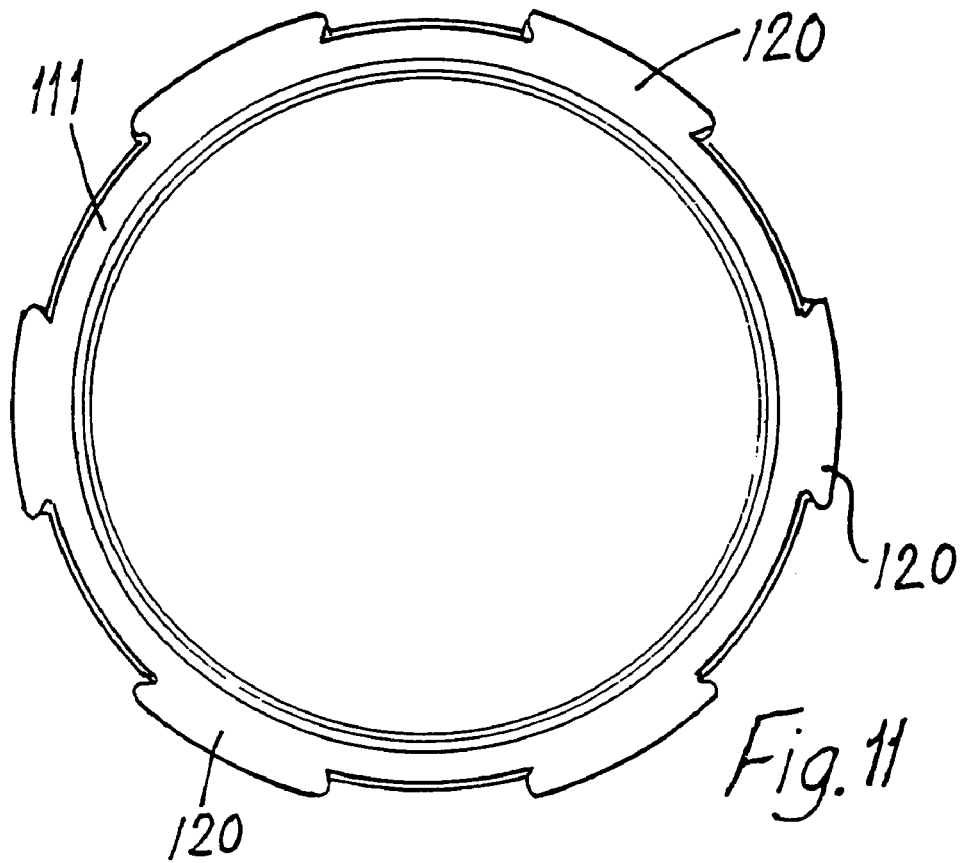
FIG. 11 is a plan view of a part of a guide means of the retractor of FIG. 2.
Figure 12:
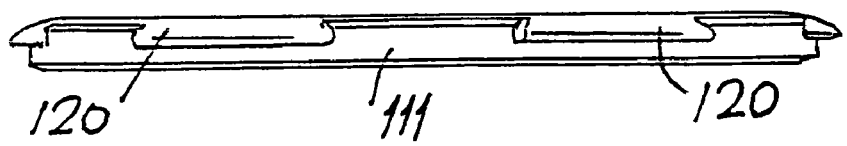
FIG. 12 is a side view of the part of FIG. 11.

The sleeve 106 is then pulled while pushing the ring parts 110, 111 against the tissue surrounding the wound opening 103, as illustrated in FIG. 8(*a*), to shorten the axial extent of the sleeve 106 and thereby bias the wound engaging portion into the retracting configuration to retract laterally the right-hand side (as viewed in FIG. 8(*a*)) of the wound opening 103. The right-hand side of the outer O-ring 109 is hooked around the formations 120 to maintain the right-hand side of the wound opening 103 retracted (FIG. 8(*b*)). The left-hand side of the sleeve 106 is then pulled while pushing the ring parts 110, 111 to retract laterally the left-hand side of the wound opening 103, as illustrated in FIG. 8(*b*). The left-hand side of the outer O-ring 109 is then hooked around the formations 120 to maintain the entire wound opening 103 fully retracted, as illustrated in FIGS. 9 and 10.

The separate formations 120 and the configuration of the wound retractor 101 generally allow the sleeve 106 to be readily manipulated locally as illustrated in FIGS. 8(*a*) and 8(*b*) to provide an optimised retraction force. Thus, the manipulation is not simply limited to a single vertical axis but can be carried out in several different directions by pulling of the sleeve 106, and localised hooking of the outer O-ring 109 to the appropriate formation 120. In this way the retractor 101 can be tailored to a particular application.

Figure 13:
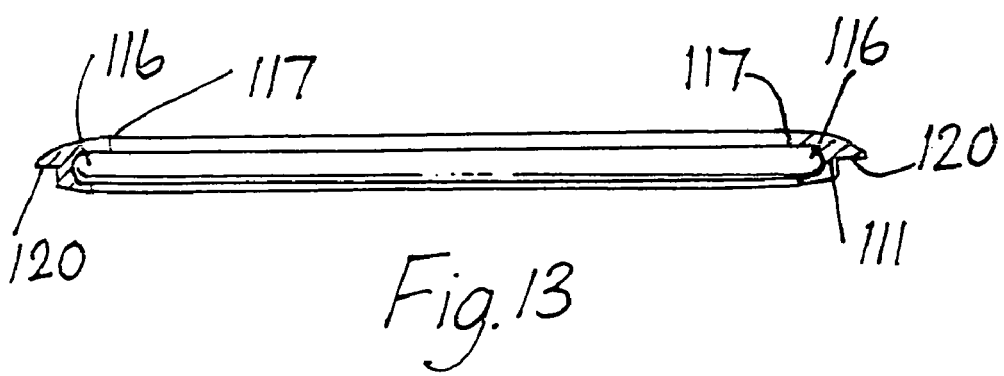
FIG. 13 is a cross sectional view along the line A-A in FIG. 11.

The recess 116 against which the sleeve 106 is slidably retained by the inner ring part 110 is C-shaped with an extended upper lip 117, as may be seen in FIG. 13. The upper lip 117 maintains the inner ring part 110 safely within the recess 116 regardless of the pulling direction or tensile pulling force exerted on the sleeve 106.

It is preferable to pull the sleeve 106 in a non-vertical direction and to perform localised hooking of the outer O-ring 109, and the extended upper lip 117 encourages non-vertical pulling of the sleeve 106.

The elastomeric sleeve 106 lines the side of the retracted wound opening 103, as illustrated in FIG. 9, and thus acts both as a means of wound retraction and wound protection.

The surgical wound retractor is of simple construction, is easy to use and can be manufactured inexpensively to provide a disposable unit.

A single wound retractor according to the invention may be used for a wide range of incision sizes and to achieve a range of different localised retraction forces which are required to accommodate the incision, the patient anatomy and the surgical procedure to be performed.

Figure 14:
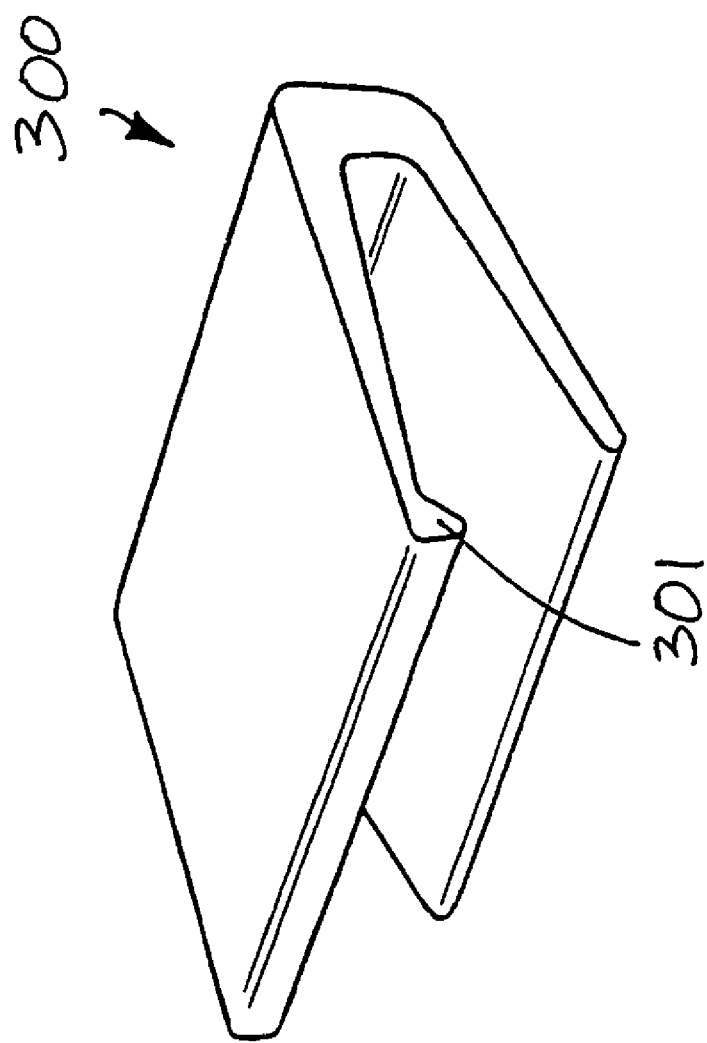
FIG. 14 is a perspective view of a clip according to the invention.

FIG. 14 illustrates a clip 300, in this case a bulldog clip, for clamping the sleeve 106 to the outer ring part 111. In this manner the clip 300 may be used to assist anchoring of the sleeve 106 in a retracted configuration and thereby maintain the wound opening 103 retracted.

The clip 300 is substantially "C"-shaped, and has an inwardly protruding shoulder 301 at the end of one arm of the C (FIG. 14).

In use, the inner O-ring 105 and the sleeve 106 are inserted into the wound opening 103, the right-hand side (as viewed in FIGS. 15 to 17) of the sleeve 106 is pulled to retract the right-hand side of the wound opening 103, and the right-hand side of the outer O-ring 109 is hooked around the formations 120 to maintain the right-hand side of the wound opening 103 retracted, in a manner similar to that described previously with reference to FIGS. 4 to 8(b).

The clip 300 is then mounted to the ring parts 110, 111 to clamp the sleeve 106 to the proximal surface of the outer ring part 111, as illustrated in FIGS. 16 and 17. In this way the clip 300 assists in ensuring the right-hand side of the wound opening 103 remains retracted.

The shoulder 301 assists in securing the clip 300 in position mounted to the outer ring part 111.

The left-hand side of the O-ring 109 is then pulled to retract the left-hand side of the wound opening 103, and the left-hand side of the O-ring 109 is hooked around the formations 120 to maintain the left-hand side of the wound opening 103 retracted, in a manner similar to that described previously with reference to FIGS. 8(b) to 10.

Further clips 300 may be mounted to the ring parts 110, 111 to assist in anchoring the wound opening 103 in the fully retracted configuration.

It will be appreciated that the clips 300 may be mounted to the ring parts 110, 111 at any suitable points around the circumference of the ring parts 110, 111. In particular it is not essential that the clip 300 be mounted to the outer ring part 111 at the anchor formation 120.

Because the clips 300 are separate components from the ring parts 110, 111, this provides an operator with enhanced operational freedom. In particular the retraction force applied to particular points of the wound opening 103 may be tailored by a suitable selection of the number and location of the clips 300.

Figure 19:
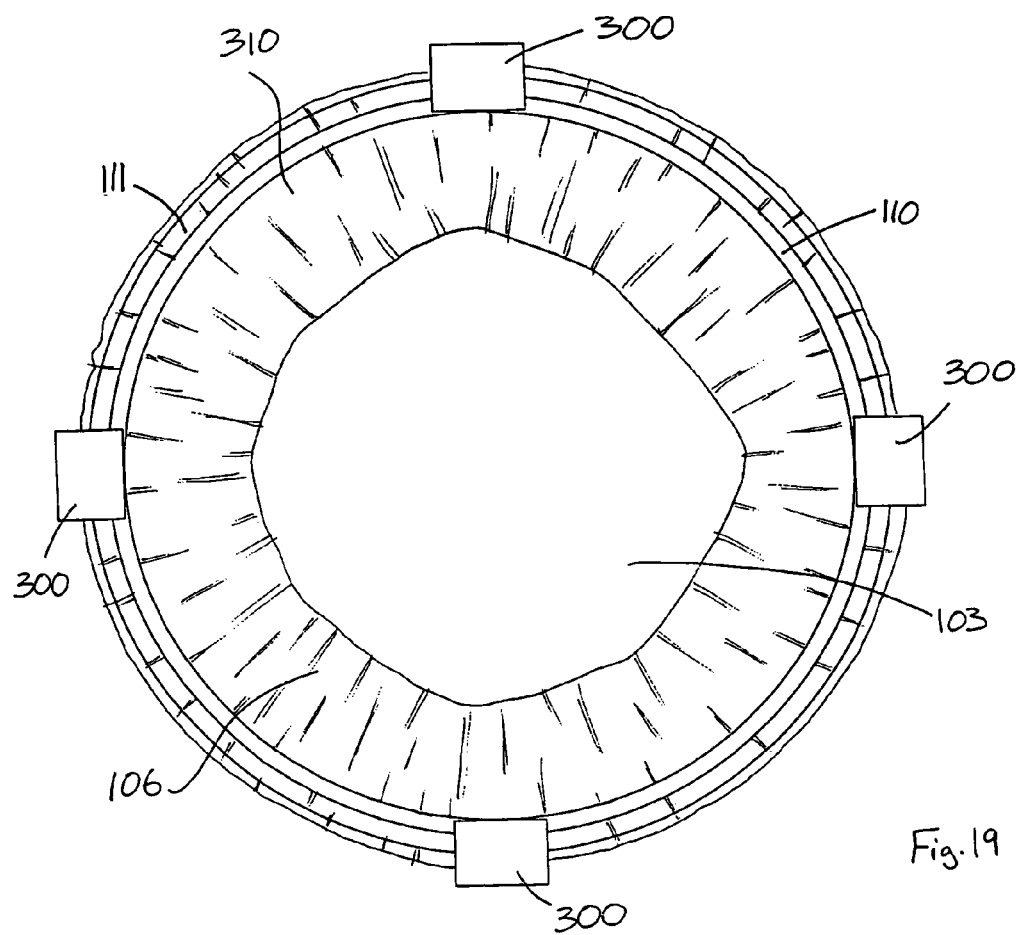
FIG. 19 is a plan view of four of the clips of FIG. 14 mounted to the retractor of FIG. 18.
Figure 18:
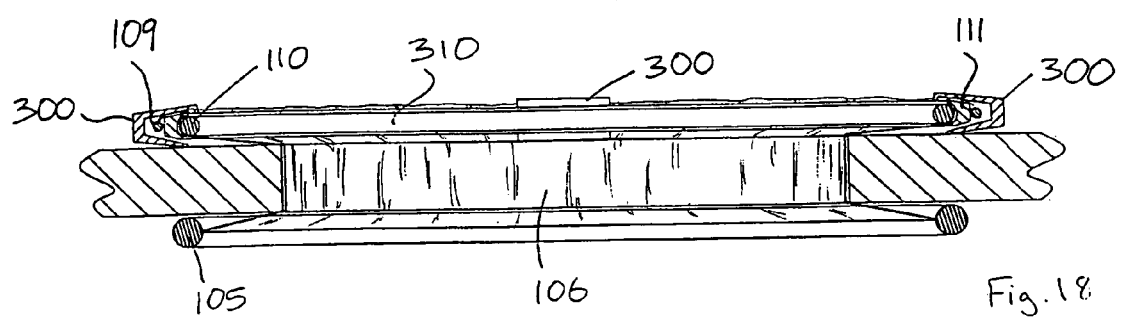
FIG. 18 is a cross-sectional, side view of four of the clips of FIG. 14 mounted to another wound retractor according to the invention.

In FIGS. 18 and 19 there is illustrated another wound retractor 310 according to the invention, which is similar to the wound retractor 101 of FIGS. 1 to 13, and similar elements in FIGS. 18 and 19 are assigned the same reference numerals.

In the case of the wound retractor 310, the outer ring part 111 has no anchor formations. The outer surface of the outer ring part 111 is smooth, as illustrated in FIG. 18.

In use the outer O-ring 109 is pulled over the outer ring part 111, and the clips 300 are mounted to the ring parts 110, 111 to clamp the sleeve 106 to the proximal surface of the outer ring part 111. In this case the clips 300 provide the only means of anchoring the sleeve 106 to maintain the wound opening 103 in the retracted configuration, as illustrated in FIG. 19.

Four clips 300 are illustrated in FIGS. 18 and 19 mounted to the ring parts 110, 111 equi-spaced around the circumference of the ring parts 110, 111. However it will be appreciated that any suitable number of clips 300 may be mounted to the ring parts 110, 111 at any suitable points around the circumference of the ring parts 110, 111 to achieve the desired anchoring of the sleeve 106.

Figure 21:
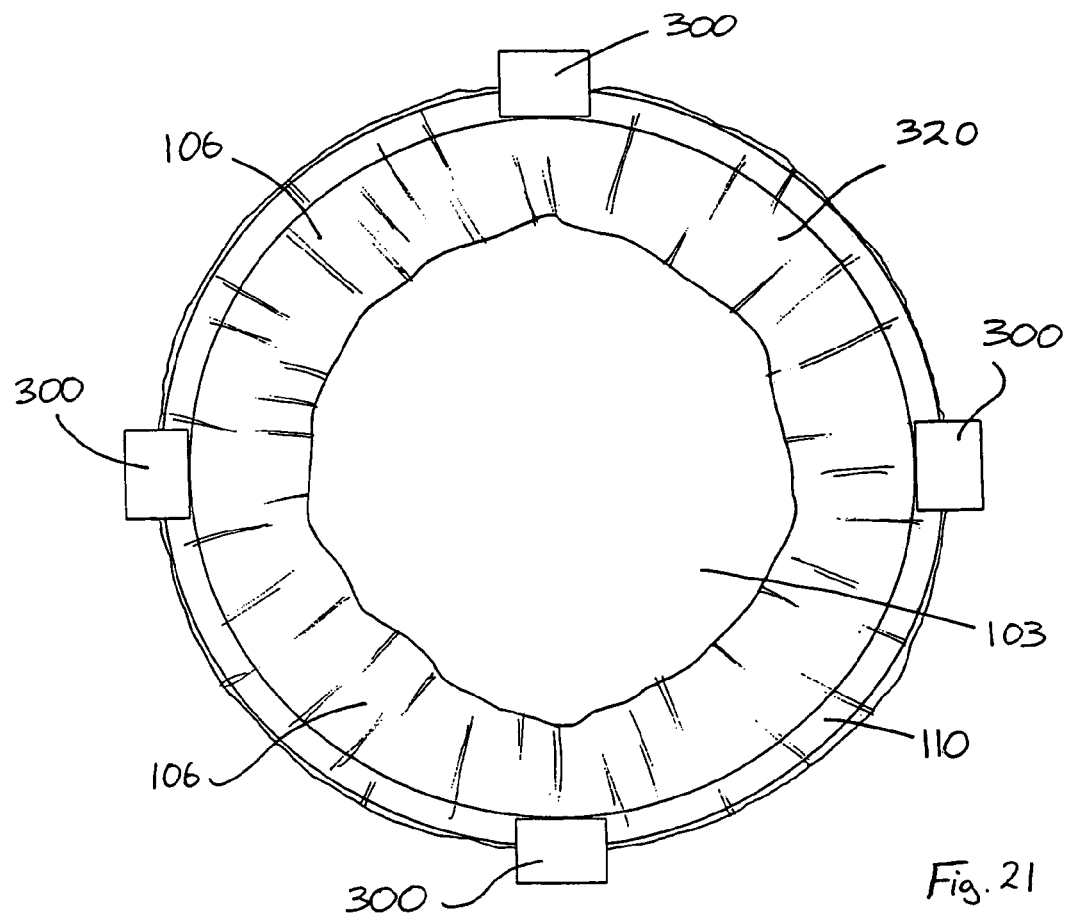
FIGS. 20 and 21 are views similar to FIGS. 18 and 19 of another wound retractor according to the invention.
Figure 20:
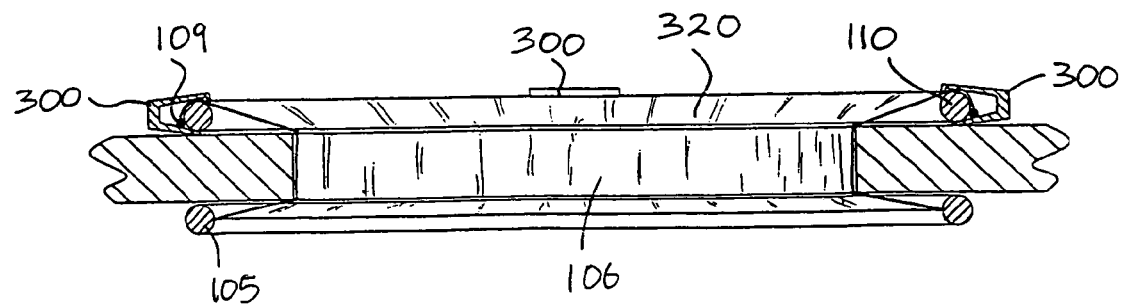

FIGS. 20 to 22 illustrate a further wound retractor 320 according to the invention, which is similar to the wound retractor 310 of FIGS. 18 and 19, and similar elements in FIGS. 20 to 22 are assigned the same reference numerals.

In the case of the wound retractor 320, the external guide means comprises the inner ring part 110 only. There is no outer ring part provided in this case, as illustrated in FIG. 20.

In use the outer O-ring 109 is pulled over the ring part 110, and the clips 300 are mounted to the ring part 110 to clamp the sleeve 106 to the proximal surface of the ring part 110. The clips 300 provide the only means of anchoring the sleeve 106 to maintain the wound opening 103 in the retracted configuration, as illustrated in FIG. 21.

Any suitable number of clips 300 may be mounted to the ring part 110 at any suitable points around the circumference of the ring part 110 to achieve the desired anchoring of the sleeve 106.

As illustrated in FIG. 22 the number and location of the clips 300 may be selected by the operator to achieve a desired retraction force at a particular point of the wound opening 103.

It will be appreciated that the clip 300 is suitable for use with a variety of different wound retractors. In certain cases, the clip 300 provides assistance to other means of anchoring the sleeve 106 to maintain the wound opening 103 retracted. In other cases, the clip 300 provides the only means of anchoring the sleeve 106 to maintain the wound opening 103 retracted.

Referring now to FIGS. 23 to 30, there is illustrated another clip for clamping the sleeve 106 to the outer ring part 110.

In this case, the clamping clip comprises an outer clip part 330 and an inner clip part 331, the clip parts 330, 331 being substantially "C"-shaped. The outer clip part 330 is configured to overlap the inner clip part 331 so that the ring parts 110, 111 are completely enclosed within the clip when the sleeve 106 is clamped to the outer ring part 110 (FIGS. 28 and 29).

The outer clip part 330 has two inwardly protruding fingers 332 for reception in two co-operating recesses 333 in the inner clip part 331 for snap-fit assembly of the clip parts 330, 331 together.

In use, the inner O-ring 105 and the sleeve 106 are inserted into the wound opening 103, the sleeve 106 is pulled to retract the wound opening 103, and the outer O-ring is pulled over the outer ring part 111.

The clip parts 330, 331 are then mounted to the ring parts 110, 111 and snap-fitted together with the inner clip part 331 along the interior of the ring parts 110, 111 and the outer clip part 330 along the exterior of the ring parts 110, 111.

The inner clip part 331 clamps the sleeve 106 to both the proximal surface of the outer ring part 111 and to the distal surface of the outer ring part 111 (FIG. 29). In this way the clip anchors the sleeve 106 to maintain the wound opening 103 retracted.

The snap-fit assembly of the ring parts 110, 111 together assists in maintaining the position of the inner clip part 331 clamping the sleeve 106 to the outer ring part 111.

It will be appreciated that any suitable number of clips may be mounted to the ring parts 110, 111 at any suitable points around the circumference of the ring parts 110, 111 to achieve the desired anchoring of the sleeve 106.

As illustrated in FIGS. 28 and 29, the outer O-ring is not hooked around the formations 120 on the outer ring part 111. When the clip parts 330, 331 are mounted to the ring parts 110, 111, the outer O-ring 109 remains outside of the assembled clip which encloses the ring parts 110, 111.

In FIGS. 23 to 30, the clip is illustrated in use with the wound retractor 101 described previously with reference to FIGS. 1 to 13. It will be appreciated however that the clip is also suitable for use with other wound retractors, such as the wound retractor 310 of FIGS. 18 and 19, or the wound retractor 320 of FIGS. 20 to 22.

Figure 31:
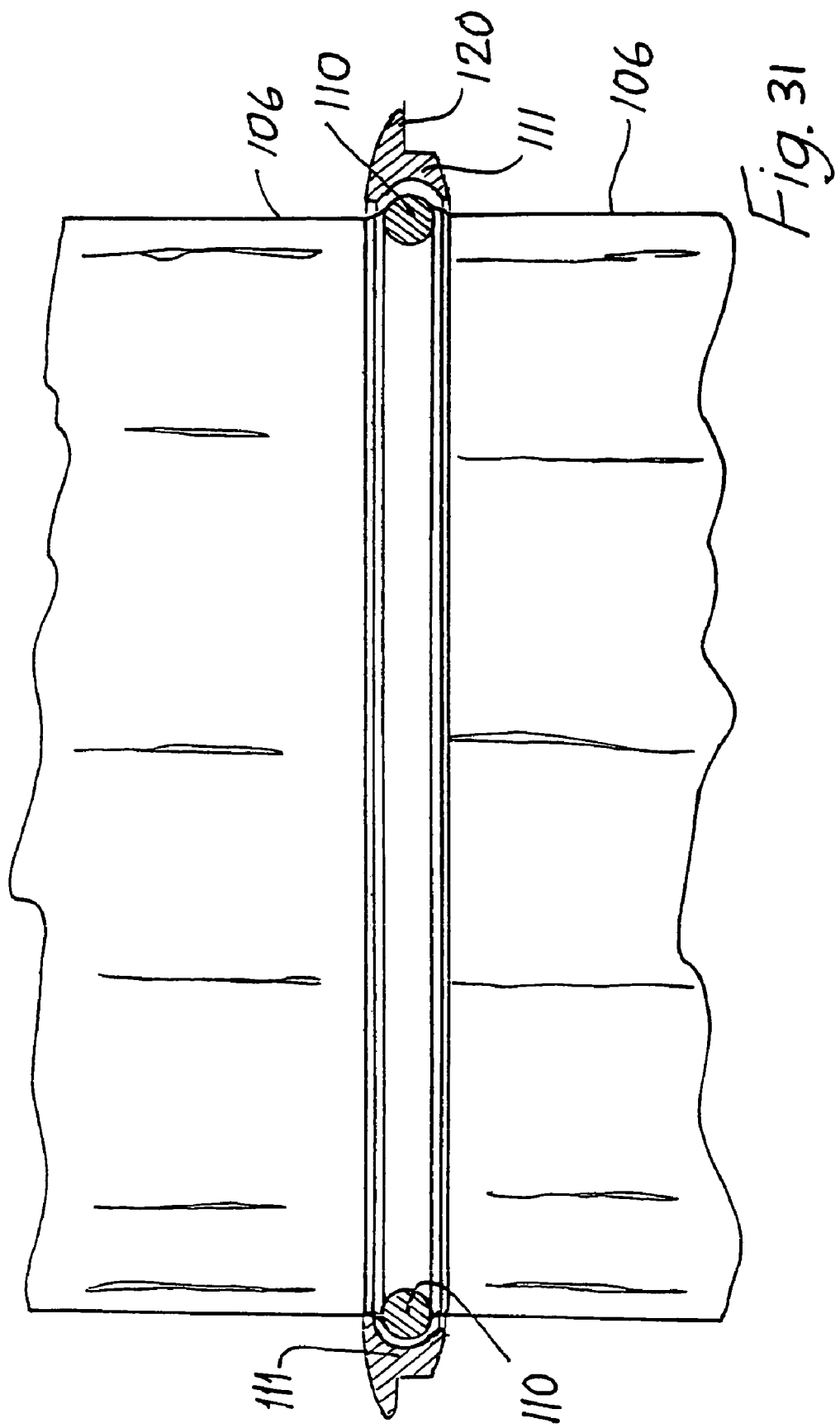
FIG. 31 is a cross sectional view of part of another wound retractor according to the invention.
Figure 32:
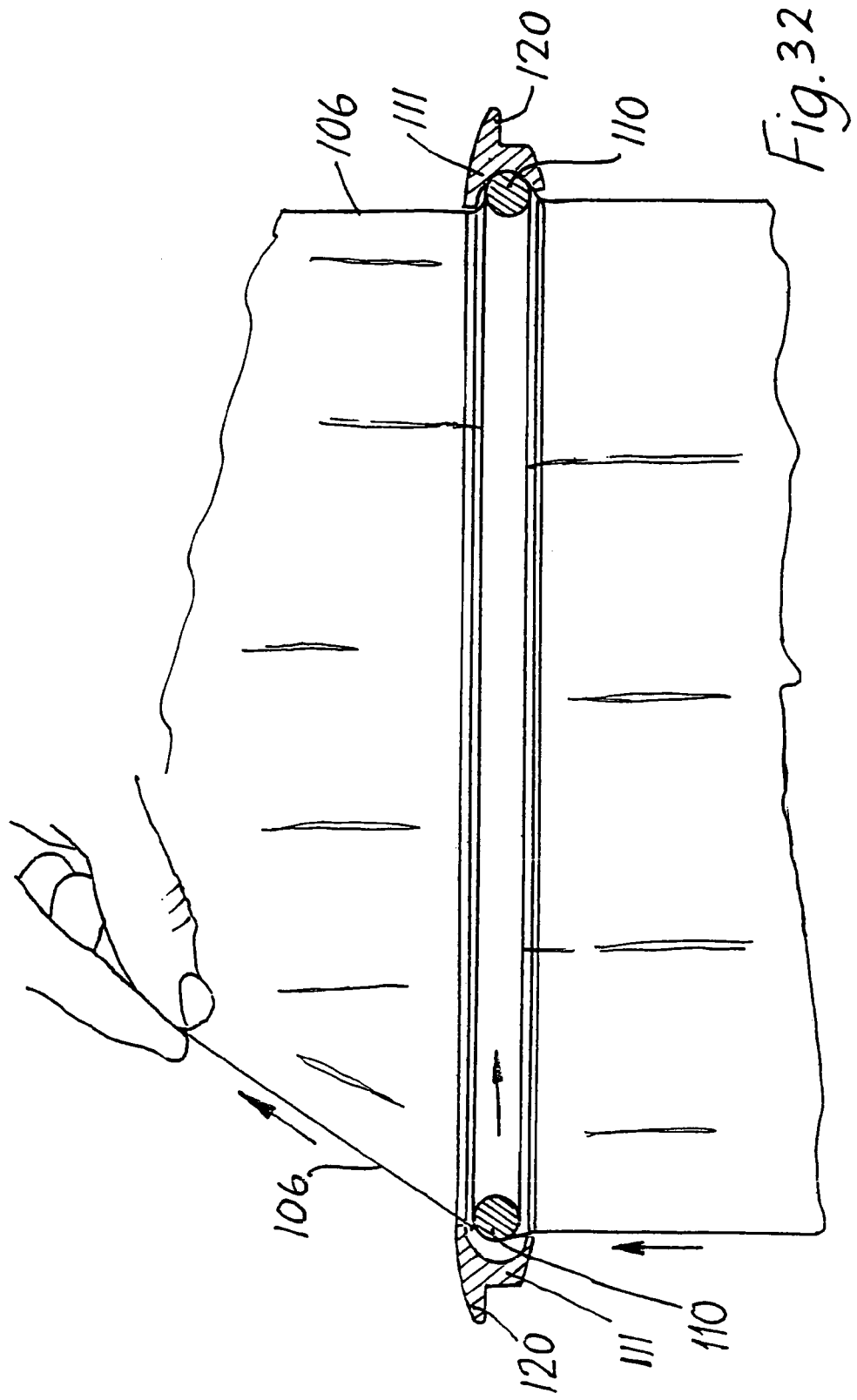
FIG. 32 is a cross sectional view of the retractor of FIG. 31, in use.
Figure 33:
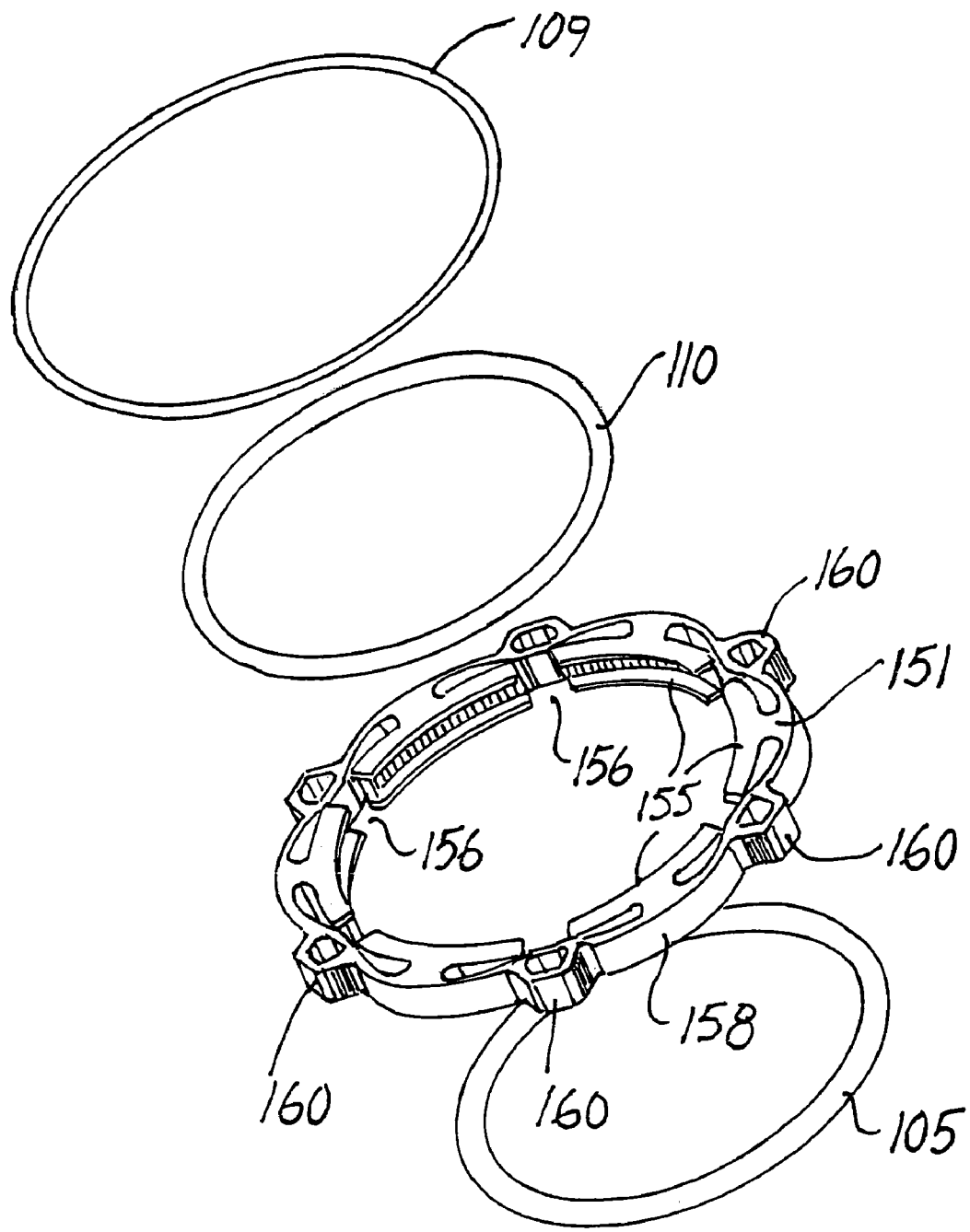
FIG. 33 is an exploded view of parts of another wound retractor according to the invention.
Figure 34:
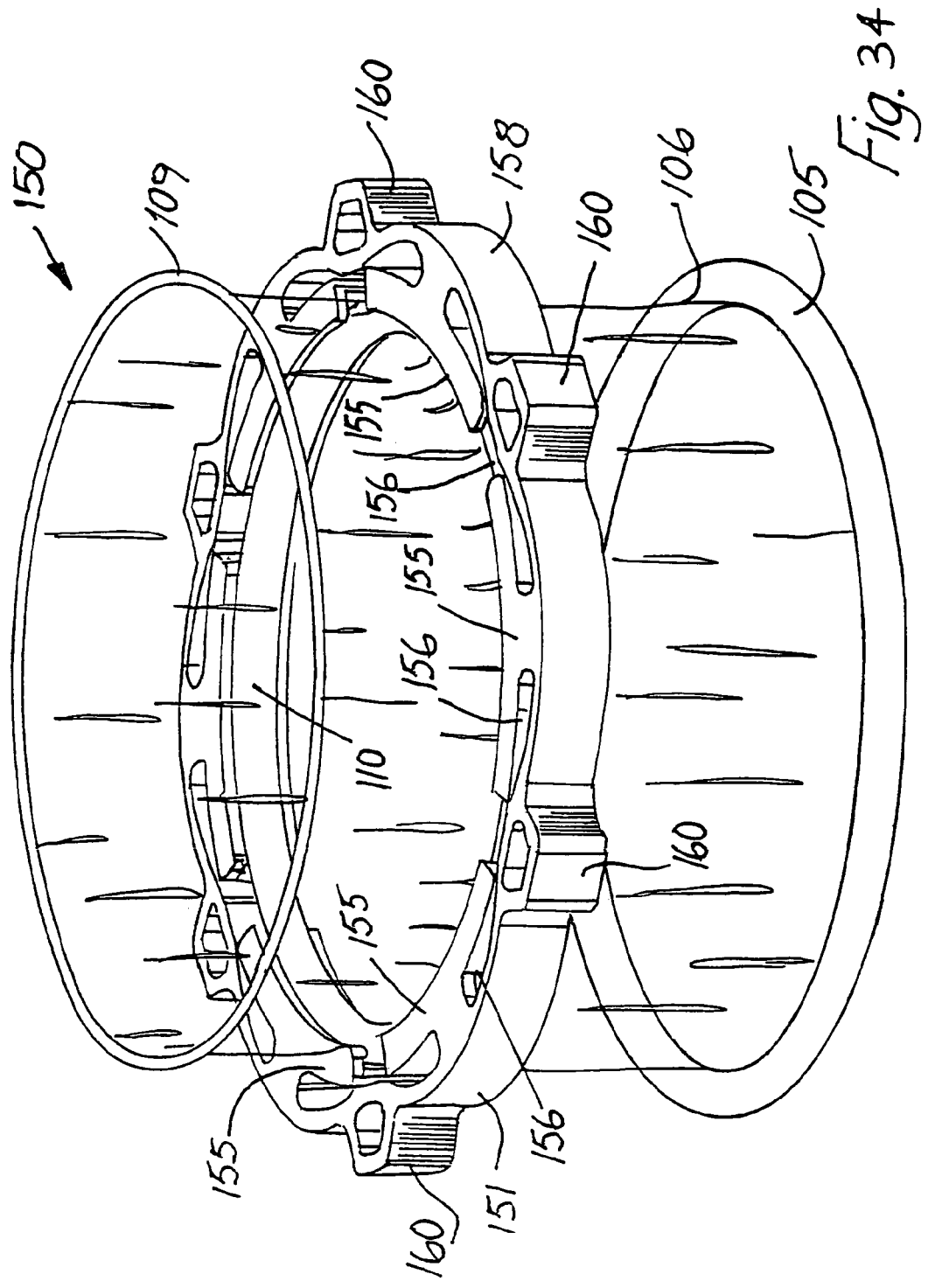
FIG. 34 is a perspective view of the wound retractor of FIG. 33 assembled.
Figure 35:
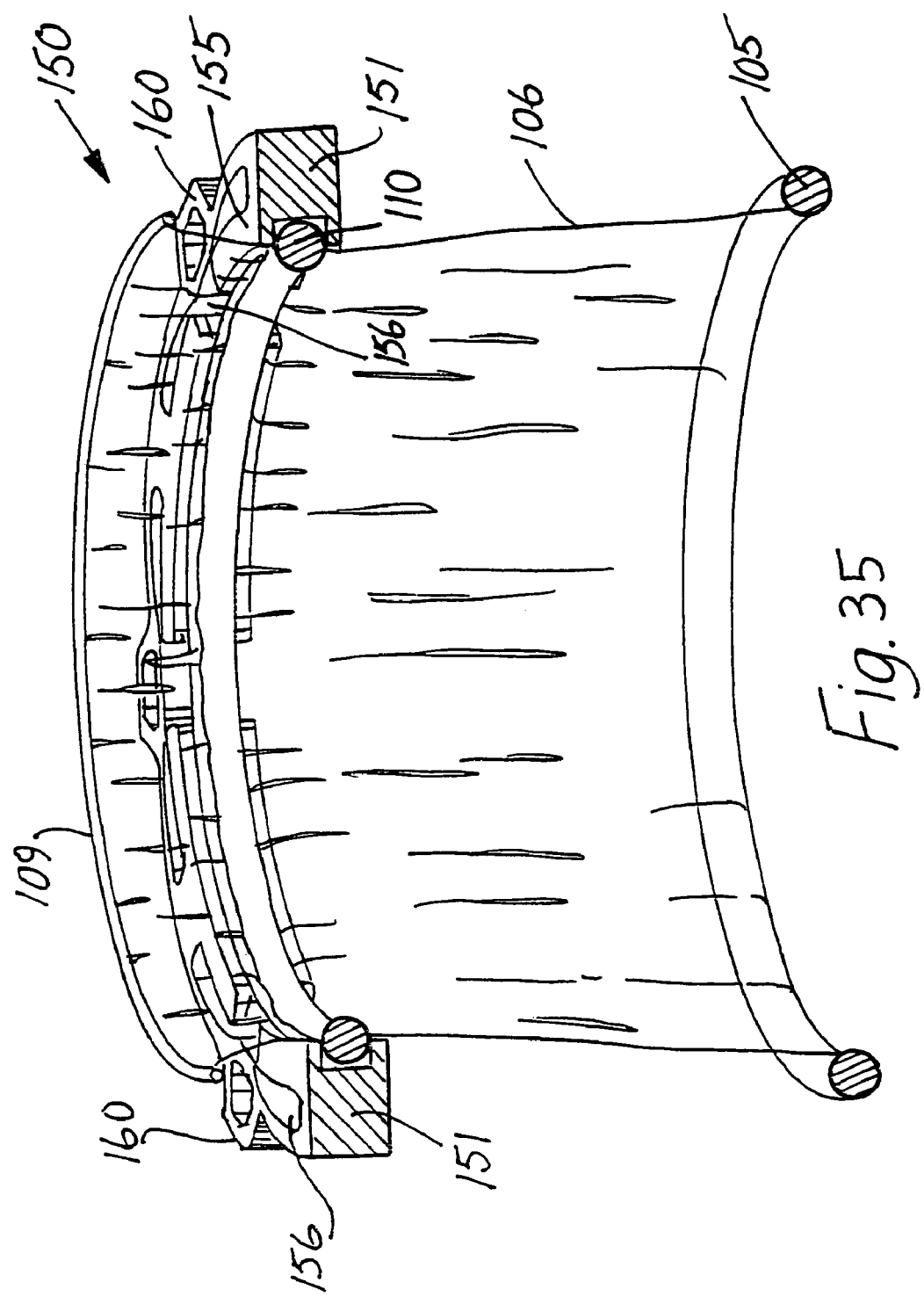

In the retractor of FIGS. 1 to 10 the sleeve 106 is a relatively tight fit between the outer and inner guide ring parts 110,111. It is also possible to configure the outer and inner ring parts 110, 111 so that the inner ring part 110 is a relatively looser fit in the outer part 111. In this case the guide means comprises an outer ring part or other annular shape within which slides a second component. The second component is of the same annular shape as the outer ring part but with a lesser diameter and has an exterior compartmental recess designed so that the outer ring part fits loosely around the second component and both can easily slide relative to each other. The components fit loosely together so that an elastomeric sleeve can fit in the gap between them and slide therein. Such an arrangement is illustrated in FIGS. 31 and 32. On pulling of a local area of the sleeve 106 as indicated in FIG. 32 the inner ring part 110 moves to the opposite side clamping the sleeve 106 at that opposite side while allowing local manipulation of the gripped section of sleeve 106 allowing the local retraction force at the gripped side to be optimised prior to anchoring of the sleeve 106 at that side. This procedure may be repeated at other local regions of the sleeve 106.

Referring to FIGS. 33 to 40 there is illustrated another wound retractor 150 according to the invention which is similar to the wound retractor 101 described with reference to FIGS. 1 to 13 and like parts are assigned the same reference numerals in FIGS. 33 to 40.

In this case the guide means comprises the inner ring part 110 and an outer PTFE ring part 151 configured so that the outer ring part 151 engages the inner ring part 110 at a plurality of discrete points circumferentially spaced around the outer ring part 151 to clamp the sleeve 106 between the inner and outer ring parts 110, 151 at each discrete point. The outer ring part 151 comprises a plurality of interconnected segments 155 circumferentially spaced around the outer ring part 151 which press on the inner ring part 110 to clamp the sleeve 106 and are independently movable to facilitate localised release of the sleeve 106 for adjustment of the retraction force.

Cut-out T-slots 156 are provided between the segments 155 and a main body 158 of the outer ring part 151, and handles 160 project radially outwardly of the main body 158 of the outer ring part 151 intermediate the segments 155.

In use, adjacent handles 160 are manually gripped as illustrated in FIG. 37 to apply a release force in the direction of arrows A which in turn pulls the local segment 155 in the direction of arrow B from a rest position clamping the sleeve 106 (FIGS. 37 and 38) to a release position (FIGS. 39 and 40) in which the sleeve 106 is readily pulled and manipulated locally. By releasing the clamp between the inner ring part 110 and the segment 155 the elastomeric sleeve 106 in readily slid from one position to another. This arrangement is particularly advantageous to facilitate local manipulation of the retraction force.

In general, the wound retractor 150 according to the invention is employed by inserting the inner O-ring 105 into a wound opening 103 and pulling the sleeve 106 so that the inner O-ring 105 lies flat against the interior anatomical surface. The inner O-ring 105 anchors the retractor 150 in the wound and prevents the elastomeric sleeve 106 from slipping out of the wound opening 103. The guide means clamp is then released by squeezing handles 160 and the ring parts 110, 151 are slid down the elastomeric sleeve 106 until they come into contact with the exterior anatomical surface. Retraction is achieved by pulling the sleeve 106 to shorten the distance between the inner O-ring 105 and the ring parts 110, 151 and thereby displace the elastomeric sleeve 106 laterally and with it the margins of the wound opening 103. The elastomeric sleeve 106 is anchored to maintain retraction of the wound opening 103 by releasing the handles 160 of the outer ring part 151 to clamp the sleeve 106.

Figure 41:
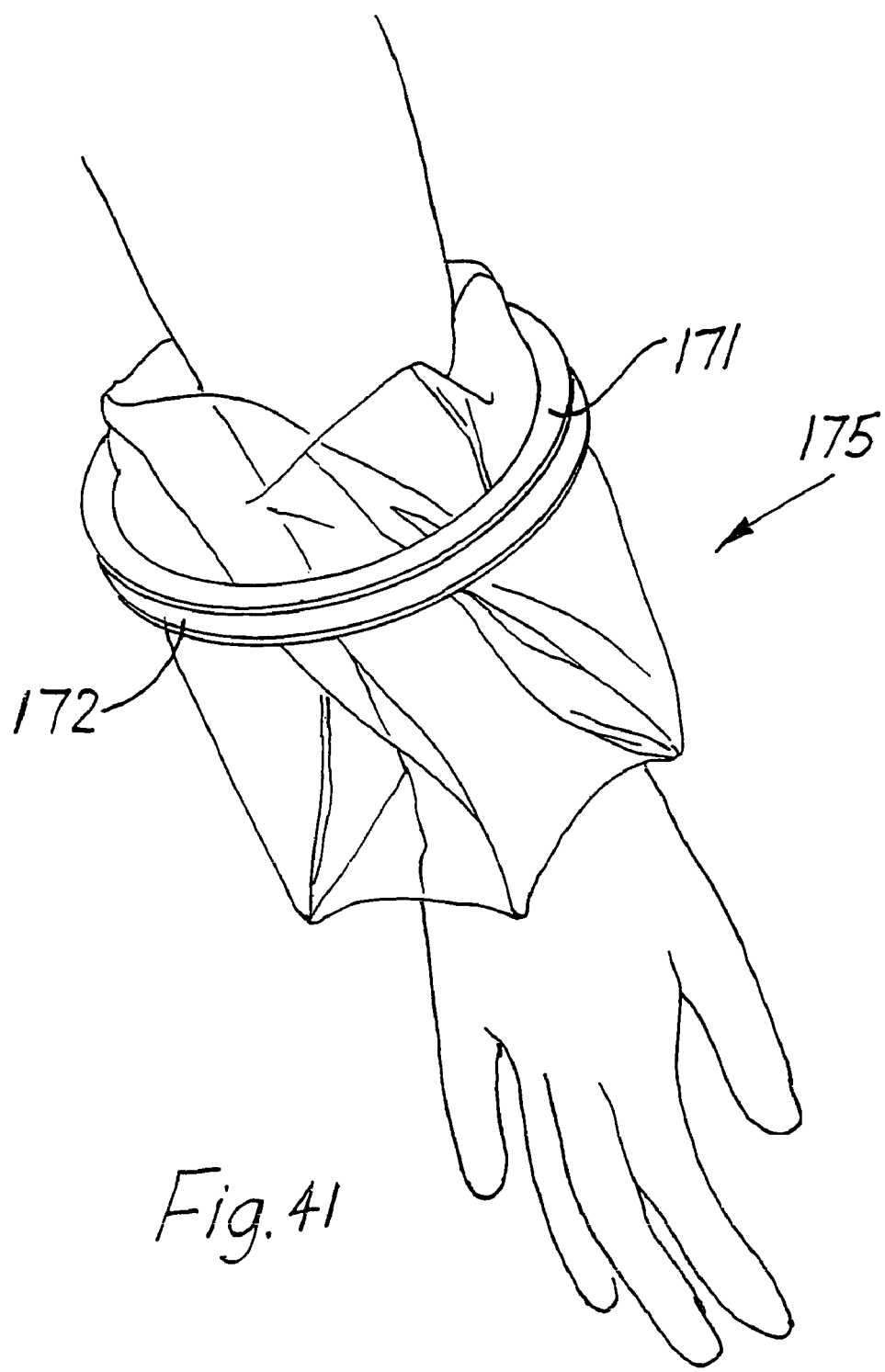
FIG. 41 is a perspective view of a hand access device for use with a wound retractor according to the invention.
Figure 42:
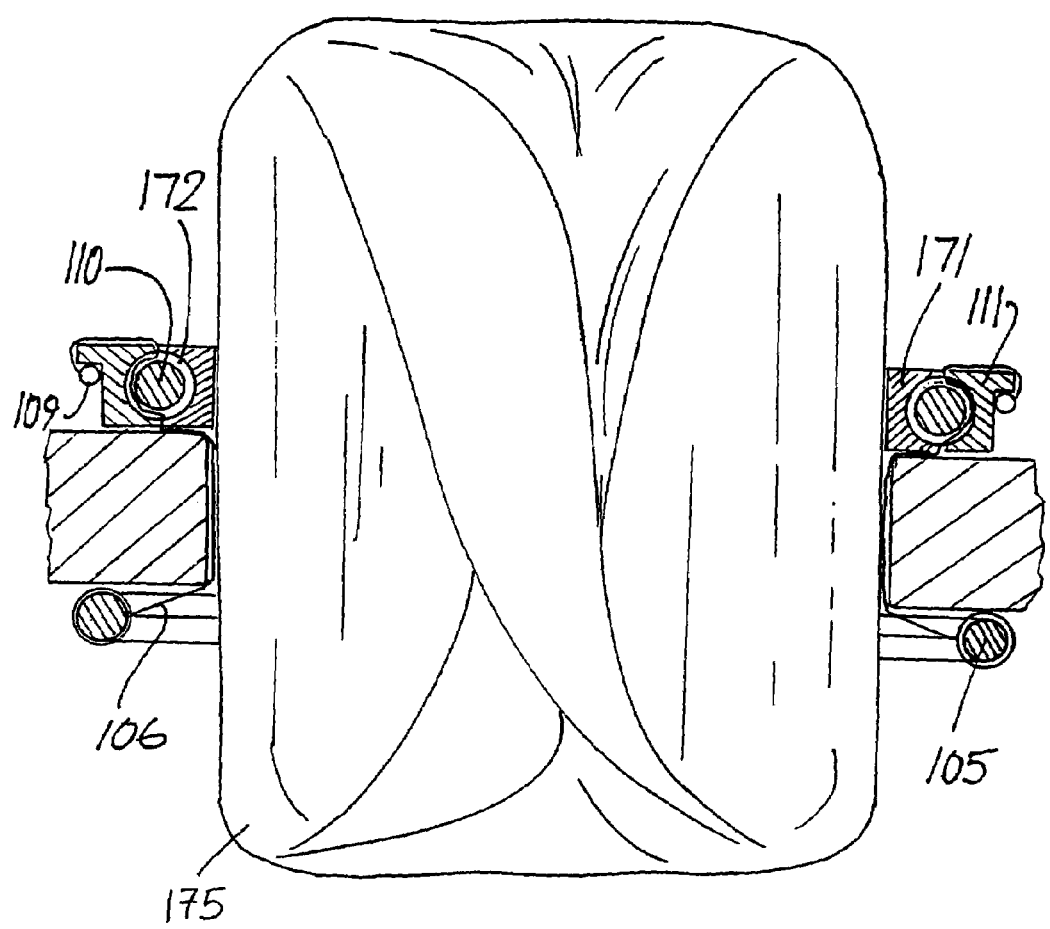
FIG. 42 is a side cross sectional view of the retractor of FIG. 2 with the hand access device of FIG. 41 in position.
Figure 43:
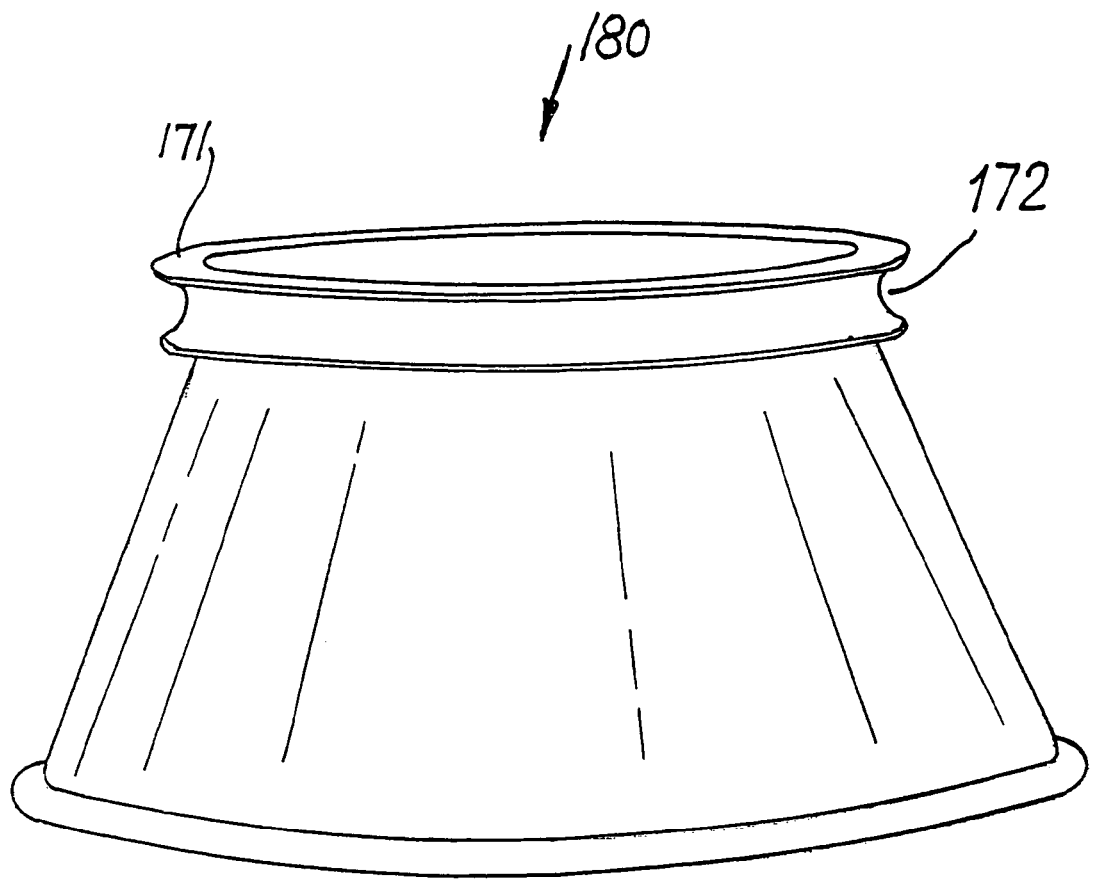
FIG. 43 is a perspective view of a drape for use with a wound retractor according to the invention.
Figure 44:
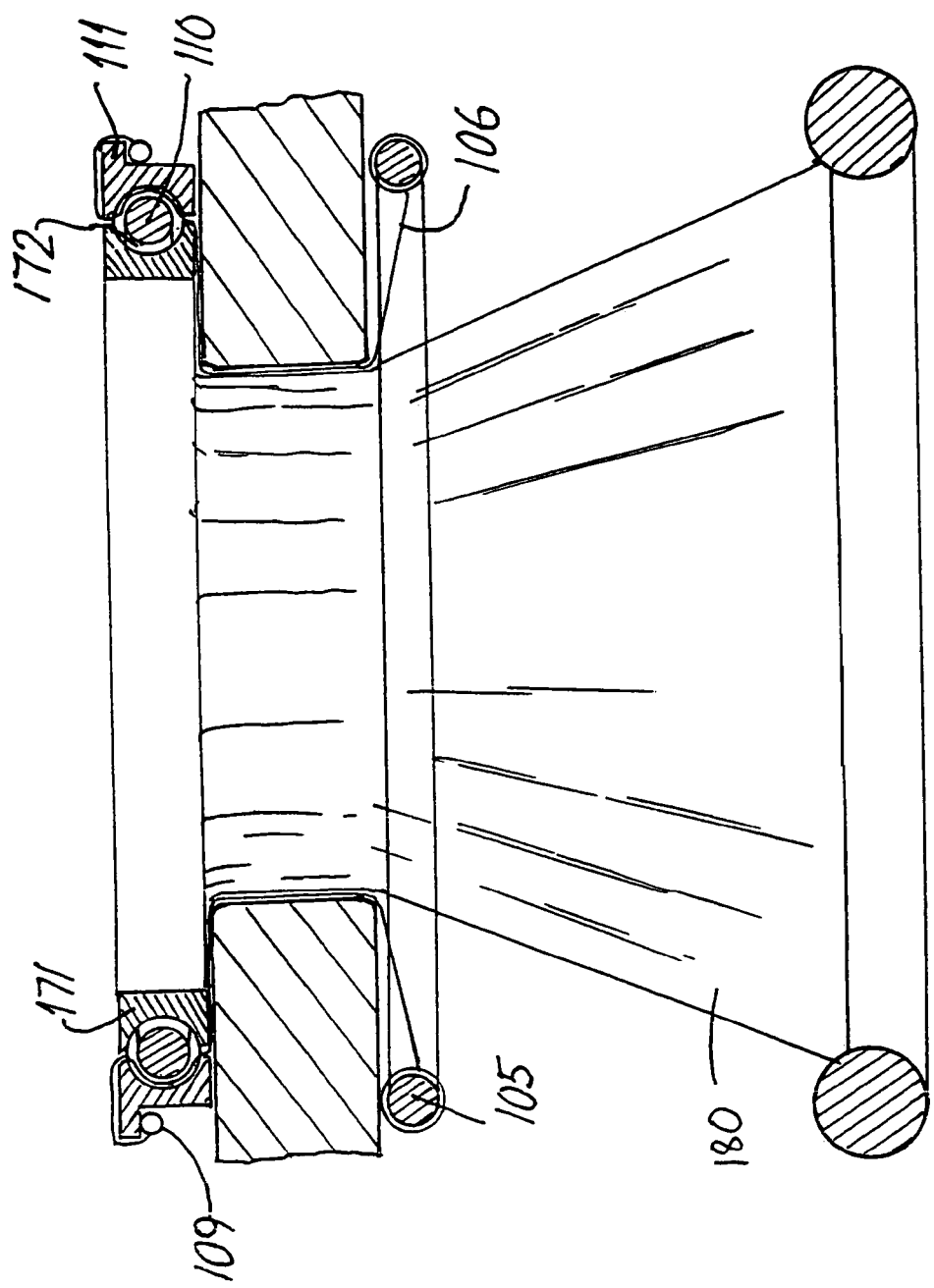
FIG. 44 is a side cross sectional view of the retractor of FIG. 2 with the drape of FIG. 43 in position.
Figure 47:
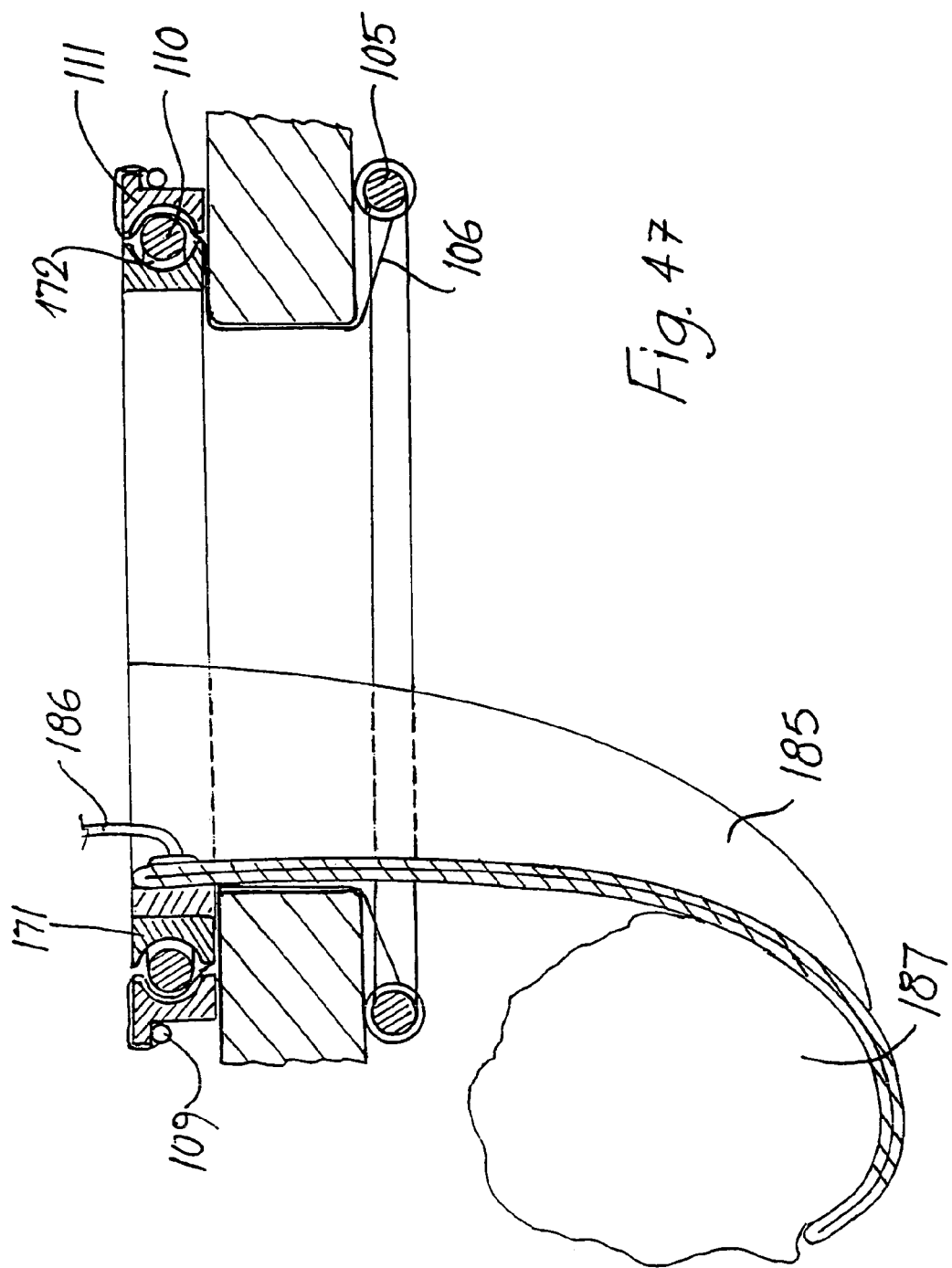
FIG. 47 is a side cross sectional view of the retractor of FIG. 2 with the stiffened form retaining device of FIG. 46 in position.

The wound retractors according to the invention also provide a platform on which a wide range of devices may be mounted. In one case the platform is provided by an inner projection part of the inner ring part 110 on which a ring part 171 with a complementary recess 172 may be easily fitted somewhat in the manner of a snap-type engagement. Various devices may be provided with such a ring part 171. For example, as illustrated in FIGS. 41 and 42 the device may be a hand access device 175 for use in laparoscopic surgery. Alternatively the device may be a drape 180 (FIGS. 43 and 44) or a form retaining device 185 which is manipulated to the form of, for example, an organ 187 to be held back and from which air is then evacuated along an evacuation line 186 to retain the desired organ holding configuration (FIGS. 45 to 47).

Figure 48:
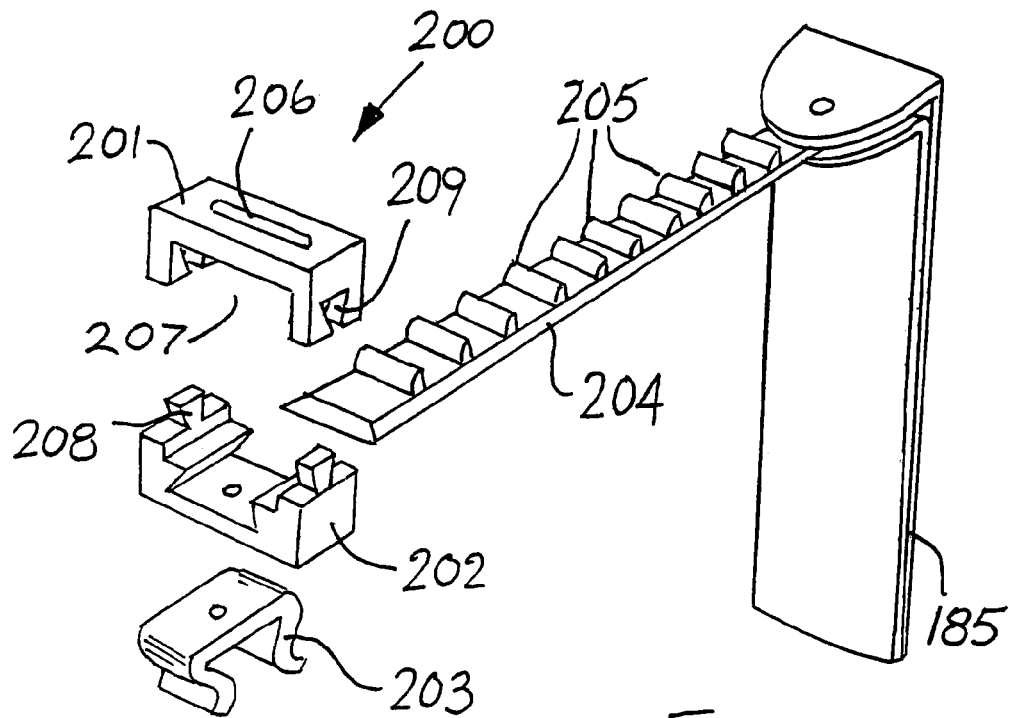
FIG. 48 is an exploded view of the form retaining device of FIG. 45 and a clamp.
Figure 49:
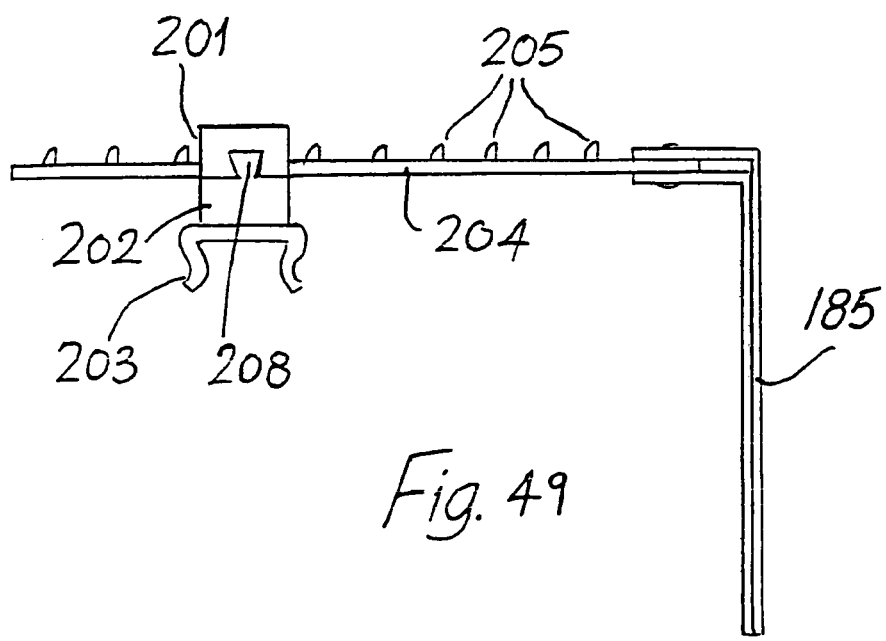
FIG. 49 is a side view of the form retaining device of FIG. 45 and the clamp of FIG. 48.
Figure 50:
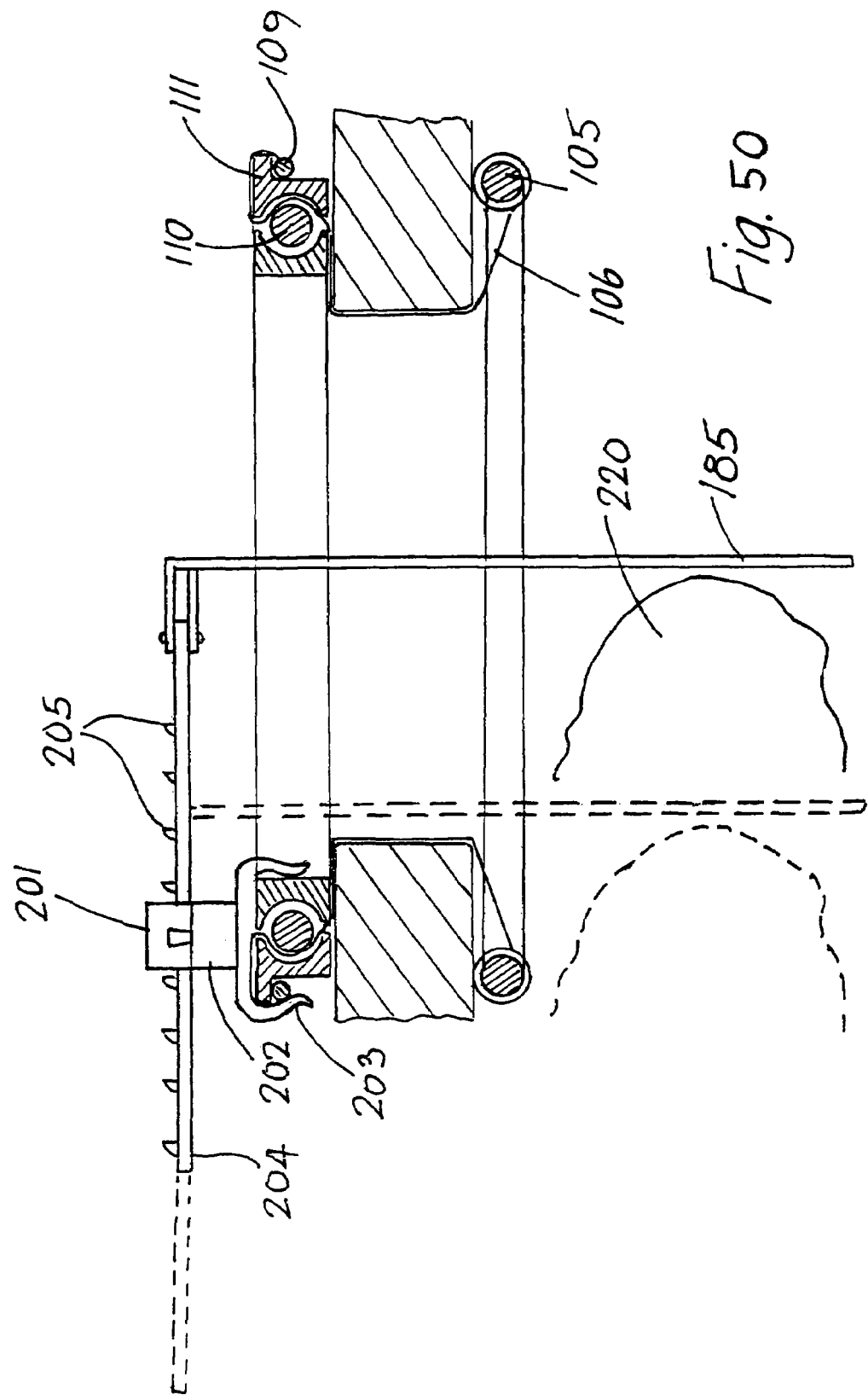
FIG. 50 is a side cross sectional view of the retractor of FIG. 2 with the form retaining device of FIG. 45 and the clamp of FIG. 48 in position.

The platform may alternatively be provided by a clamp 200 as illustrated in FIGS. 48 to 50. The clamp 200 comprises an upper jaw 201, a lower jaw 202, a clip 203 and an arm 204.

The clamp 200 is assembled by screwing the clip 203 to the base of the lower jaw 202, sliding the upper jaw 201 over the lower jaw 202 to engage the male projecting parts 208 within the corresponding female recesses 209 and extending the arm 204 through the open mouth 207 between the upper and lower jaws 201, 202. A plurality of teeth 205 are provided on the arm 204, the teeth 205 being sized to project upwardly through a recess 206 in the upper jaw 201 when the arm 204 is within the open mouth 207. The teeth 205, as shown more clearly in FIG. 49, are shaped such that the arm 204 may be pulled back through the open mouth 207 in a ratchet-type arrangement but cannot be pushed forward again. A suitable material for the clamp components 201, 202, 203, 204 is spring steel.

Various devices may be attached to the free end of the arm 204, such as the form retaining device 185, as illustrated in FIG. 48. In use, the clip 203 is securely fixed to the wound retractor 101 by a snap-fit arrangement with the form retaining device 185 extending into the wound opening 103, as illustrated in FIG. 50. The form retaining device 185 is then ratcheted laterally across the wound opening 103 to retract, for example, an internal organ 220. The ratchet configuration of the clamp 200 and the rigidity of the form retaining device 185 ensure that the internal organ 220 is securely maintained in a desired position.

It will be appreciated that any of the embodiments of the wound retractor according to the invention and/or the clips for clamping the sleeve may be used as a platform on which to mount other devices for use in various surgical procedures. Such devices may include: a capping device to cover the incision site or orifice; a hand-access device to allow the surgical procedure to be converted from an open procedure into a hand-assisted laparoscopic procedure; an instrument port for the insertion of instruments; a trocar for use in laparoscopic surgery; an internal organ retractor to assist in the displacement of internal structures from the operative field; or an illuminating means to deliver illumination to an area shaded from the theatre lights. It will be clear to those skilled in the art that the enhancements are not limited to the brief list mentioned here.

The wound retractor may be constructed in other annular shapes. For example the distal and proximal rings attached to the elastomeric sleeve may be oval or elliptical instead of circular.

The retractor may be used to retract and protect the margins of a natural bodily orifice such as the anus or vagina, or can be used to retract and protect the edges of a man-made stoma such as is created for tracheostomy or following gastrointestinal surgery.

The invention is not limited to the embodiments hereinbefore described which may be varied in both construction and detail.

The invention claimed is:

1. A wound retractor device, comprising:
   a longitudinal axis;
   a distal ring;
   a proximal assembly including a first member having a radially inner portion and a radially outer portion, and a second member having a radially inner portion and a radially outer portion, the second member including a plurality of interconnected segments which are independently movable to facilitate localized release of the sleeve; and
   a wound retracting sleeve extending at least between the distal ring and the proximal assembly and slidably received between the radially outer portion of the first member and the radially inner portion of the second member.

2. A wound retractor as claimed in claim 1, wherein the sleeve is a generally cylindrical sleeve.

3. A wound retractor as claimed in claim 1, further including a securing portion configured to fix the sleeve at a desired axial length between the distal ring and the proximal assembly.

4. A wound retractor as claimed in claim 3, wherein the securing portion includes formations on the second member configured to receive a portion of the sleeve.

5. A wound retractor as claimed in claim 1, wherein at least a portion of the first member is located within a recess of the second member.

6. A wound retractor as claimed in claim 1, wherein the segments are manually manipulable between a clamped rest position and a release position.

7. A wound retractor as claimed in claim 1, wherein the distal ring is of resilient material.

8. A wound retractor as claimed in claim 1, wherein the distal ring is an O-ring.

9. A wound retractor as claimed in claim 1, wherein at least a portion of the proximal assembly includes a material with a low coefficient of friction.

10. A wound retractor as claimed in claim 9, said material with a low coefficient of friction is polytetrafluroethylene.

11. A wound retractor as claimed in claim 1, further including a sealing device coupled to the proximal assembly so as to allow the wound retractor to be used in laparoscopic surgery.

12. A wound retractor as claimed in claim 11, wherein the sealing device includes a hand access device that extends across a central opening provided by the retractor.

13. A wound retractor as claimed in claim 1, further including a capping device coupled to the proximal assembly, the capping device extending across a central opening provided by the retractor.

14. A wound retractor as claimed in claim 1, wherein the first member includes a ring having a circular cross-section.

15. A wound retractor as claimed in claim 14, wherein the second member includes a ring shape.

16. A wound retractor as claimed in claim 1, wherein the radially outer portion of the first member is curved.

17. A wound retractor as claimed in claim 1, wherein the sleeve is fixed to the distal ring.

18. A wound retractor as claimed in claim 1, further including a clamp to assist in securing the sleeve to the proximal assembly.

19. A wound retractor device, comprising:
   a longitudinal axis;
   a distal ring;
   a proximal assembly including a first member having a radially outer portion, and a second member having a radially inner portion, the radially outer portion of the first member being located at least partially within a recess in the radially inner portion; and
   a generally cylindrical wound retracting sleeve extending at least between the distal ring and the proximal assembly, through the proximal assembly between the radially outer portion of the first member and the radially inner portion of the second member, and proximally beyond the proximal assembly, a portion of the sleeve extending proximally beyond the proximal assembly forming a gripping portion for pulling the sleeve to shorten an axial length of the sleeve located between the distal ring and the proximal assembly.

20. A wound retractor as claimed in claim 19, wherein the distal ring is of resilient material.

21. A wound retractor as claimed in claim 19, wherein at least a portion of the proximal assembly includes polytetrafluroethylene.

22. A wound retractor as claimed in claim 19, further including a sealing device coupled to the proximal assembly so as to allow the wound retractor to be used in laparoscopic surgery.

23. The wound retractor as claimed in claim 22, wherein the sealing device is coupled to the proximal assembly via a snap-type engagement.

* * * * *